United States Patent
Buermann et al.

(10) Patent No.: US 11,565,267 B2
(45) Date of Patent: Jan. 31, 2023

(54) INTEGRATED OPTOELECTRONIC READ HEAD AND FLUIDIC CARTRIDGE USEFUL FOR NUCLEIC ACID SEQUENCING

(71) Applicant: Illumina, Inc., San Diego, CA (US)

(72) Inventors: Dale Buermann, San Diego, CA (US); John A. Moon, San Diego, CA (US); Bryan Crane, San Diego, CA (US); Mark Wang, San Diego, CA (US); Stanley S. Hong, Menlo Park, CA (US); Jason Harris, San Ramon, CA (US); Matthew Hage, San Diego, CA (US); Mark J. Nibbe, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 406 days.

(21) Appl. No.: 16/735,001

(22) Filed: Jan. 6, 2020

(65) Prior Publication Data
US 2020/0139375 A1    May 7, 2020

Related U.S. Application Data

(60) Continuation of application No. 15/594,413, filed on May 12, 2017, now Pat. No. 10,549,281, which is a
(Continued)

(51) Int. Cl.
*B01L 3/00* (2006.01)
*G01N 21/05* (2006.01)
(Continued)

(52) U.S. Cl.
CPC ............ *B01L 3/527* (2013.01); *C12Q 1/6869* (2013.01); *C12Q 1/6874* (2013.01);
(Continued)

(58) Field of Classification Search
None
See application file for complete search history.

(56) References Cited

U.S. PATENT DOCUMENTS

| 4,160,263 A | 7/1979 | Christy et al. |
| 5,803,117 A | 9/1998 | Olsen et al. |

(Continued)

FOREIGN PATENT DOCUMENTS

| EP | 1325298 | 9/2008 |
| JP | 2007/108154 | 4/2007 |

(Continued)

OTHER PUBLICATIONS

Bentley, et al. "Accurate whole human genome sequencing using reversible terminator chemistry", Nature, vol. 456, No. 7218, Nov. 6, 2008, pp. 53-59.

*Primary Examiner* — Robert T. Crow
(74) *Attorney, Agent, or Firm* — Illumina, Inc.

(57) ABSTRACT

A detection apparatus having a read head including a plurality of microfluorometers positioned to simultaneously acquire a plurality of the wide-field images in a common plane; and (b) a translation stage configured to move the read head along a substrate that is in the common plane. The substrate can be a flow cell that is included in a cartridge, the cartridge also including a housing for (i) a sample reservoir; (ii) a fluidic line between the sample reservoir and the flow cell; (iii) several reagent reservoirs in fluid communication with the flow cell; (iv) at least one valve configured to mediate fluid communication between the reservoirs and the flow cell; and (v) at least one pressure source configured to move liquids from the reservoirs to the flow cell. The detection apparatus and cartridge can be used together or independent of each other.

14 Claims, 18 Drawing Sheets

Related U.S. Application Data division of application No. 14/335,117, filed on Jul. 18, 2014, now Pat. No. 9,650,669, which is a division of application No. 13/766,413, filed on Feb. 13, 2013, now Pat. No. 9,193,996.

(60) Provisional application No. 61/619,784, filed on Apr. 3, 2012.

(51) Int. Cl.
*C12Q 1/6869* (2018.01)
*G01N 21/64* (2006.01)
*C12Q 1/6874* (2018.01)
*G01N 21/03* (2006.01)

(52) U.S. Cl.
CPC ..... *G01N 21/6428* (2013.01); *G01N 21/6486* (2013.01); *B01L 3/502715* (2013.01); *B01L 2200/16* (2013.01); *B01L 2300/0877* (2013.01); *B01L 2400/0487* (2013.01); *B01L 2400/06* (2013.01); *G01N 2021/0307* (2013.01); *G01N 2021/0325* (2013.01); *G01N 2021/058* (2013.01); *G01N 2021/6417* (2013.01); *G01N 2021/6441* (2013.01); *G01N 2021/6482* (2013.01)

(56) References Cited

U.S. PATENT DOCUMENTS

| | | | |
|---|---|---|---|
| 6,012,488 A | 1/2000 | Nicols | |
| 6,176,442 B1 | 1/2001 | Eicher et al. | |
| 6,320,174 B1 | 11/2001 | Tafas et al. | |
| 6,326,612 B1 | 12/2001 | Elkind et al. | |
| 6,374,684 B1 | 4/2002 | Dority | |
| 6,424,404 B1 | 7/2002 | Johnson | |
| 6,603,546 B1 | 8/2003 | Barbieri et al. | |
| 6,950,241 B1 | 9/2005 | Liang | |
| 6,982,166 B2 | 1/2006 | Sandell | |
| 7,034,317 B2 | 4/2006 | Olszak et al. | |
| 7,057,026 B2 | 6/2006 | Barnes et al. | |
| 7,116,437 B2 | 10/2006 | Weinstein et al. | |
| 7,130,115 B2 | 10/2006 | Olszak et al. | |
| 7,143,787 B1 | 12/2006 | Bauerle et al. | |
| 7,193,775 B2 | 3/2007 | Olszak et al. | |
| 7,211,414 B2 | 5/2007 | Hardin et al. | |
| 7,315,019 B2 | 1/2008 | Turner et al. | |
| 7,329,492 B2 | 2/2008 | Hardin et al. | |
| 7,329,860 B2 | 2/2008 | Feng et al. | |
| 7,330,574 B2 | 2/2008 | Olszak | |
| 7,388,714 B2 | 6/2008 | Liang et al. | |
| 7,405,281 B2 | 7/2008 | Xu et al. | |
| 7,482,566 B2 | 1/2009 | Olszak | |
| 7,547,874 B2 | 6/2009 | Liang | |
| 7,834,911 B2 | 11/2010 | Muraki | |
| 7,835,871 B2 | 11/2010 | Kain et al. | |
| 7,864,369 B2 | 1/2011 | Olszak et al. | |
| 7,998,437 B2 | 8/2011 | Berndt et al. | |
| 8,039,817 B2 | 10/2011 | Feng et al. | |
| 9,193,996 B2 | 11/2015 | Buermann et al. | |
| 2002/0062747 A1 | 5/2002 | Hashimoto et al. | |
| 2003/0036855 A1 | 2/2003 | Harris et al. | |
| 2003/0199081 A1 | 10/2003 | Wilding et al. | |
| 2004/0023284 A1 | 2/2004 | Browne | |
| 2004/0224317 A1 | 11/2004 | Kordunsky et al. | |
| 2005/0127271 A1 | 6/2005 | Ortyn et al. | |
| 2005/0221373 A1 | 10/2005 | Enzelberger et al. | |
| 2006/0177844 A1 | 8/2006 | Ching et al. | |
| 2006/0223169 A1 | 10/2006 | Bedingham et al. | |
| 2007/0280855 A1 | 12/2007 | Matteo | |
| 2008/0013092 A1 | 1/2008 | Maltezos et al. | |
| 2008/0014576 A1 | 1/2008 | Jovanovich et al. | |
| 2008/0038737 A1* | 2/2008 | Smith | C12Q 1/686 435/6.12 |
| 2008/0088918 A1 | 4/2008 | O'Connell | |
| 2008/0108082 A1 | 5/2008 | Rank et al. | |
| 2008/0117425 A1 | 5/2008 | Kain | |
| 2008/0125330 A1 | 5/2008 | Cady et al. | |
| 2008/0151363 A1 | 6/2008 | Vesa et al. | |
| 2008/0254467 A1 | 10/2008 | Regan | |
| 2008/0262172 A1 | 10/2008 | Zhao | |
| 2008/0262747 A1 | 10/2008 | Kain et al. | |
| 2009/0142846 A1 | 6/2009 | Crenshaw et al. | |
| 2009/0272914 A1 | 11/2009 | Feng et al. | |
| 2010/0157086 A1 | 2/2010 | Segale | |
| 2011/0001036 A1 | 1/2011 | Stallinga et al. | |
| 2011/0017902 A1 | 1/2011 | Hing et al. | |
| 2011/0052446 A1* | 3/2011 | Hirano | B01J 19/0046 422/68.1 |
| 2011/0059865 A1 | 3/2011 | Smith et al. | |
| 2012/0270305 A1 | 10/2012 | Reed et al. | |

FOREIGN PATENT DOCUMENTS

| | | |
|---|---|---|
| WO | WO 1991/06678 | 5/1991 |
| WO | WO 2001/23913 | 5/2001 |
| WO | WO 2004/018497 | 3/2004 |
| WO | WO 2007/123744 | 11/2007 |
| WO | WO 2011/067559 | 6/2011 |
| WO | WO 2012/027586 | 3/2012 |
| WO | WO 2012/042226 | 4/2012 |

\* cited by examiner

INTEGRATED OPTOELECTRONIC READ HEAD AND FLUIDIC CARTRIDGE USEFUL FOR NUCLEIC ACID SEQUENCING

CROSS-REFERENCE TO RELATED APPLICATIONS

This application is a continuation of co-pending U.S. application Ser. No. 15/594,413, filed May 12, 2017, which itself is a division of U.S. application Ser. No. 14/335,117, filed Jul. 18, 2014, now U.S. Pat. No. 9,650,669, which is itself a division of U.S. application Ser. No. 13/766,413, filed Feb. 13, 2013, now U.S. Pat. No. 9,193,996, which itself is based on, and claims the benefit of, U.S. Provisional Application No. 61/619,784, filed Apr. 3, 2012, each of which is incorporated herein by reference in its entirety.

BACKGROUND

Embodiments of the present disclosure relate generally to apparatus and methods for fluidic manipulation and optical detection of samples, for example, in nucleic acid sequencing procedures.

Our genome provides a blue print for predicting many of our inherent predispositions such as our preferences, talents, susceptibility to disease and responsiveness to therapeutic drugs. An individual human genome contains a sequence of over 3 billion nucleotides. Differences in just a fraction of those nucleotides impart many of our unique characteristics. The research community is making impressive strides in unraveling the features that make up the blue print and with that a more complete understanding of how the information in each blue print relates to human health. However, our understanding is far from complete and this is hindering movement of the information from research labs to the clinic where the hope is that one day each of us will have a copy of our own personal genome so that we can sit down with our doctor to determine appropriate choices for a healthy lifestyle or a proper course of treatment.

The current bottleneck is a matter of throughput and scale. A fundamental component of unraveling the blue print for any given individual is to determine the exact sequence of the 3 billion nucleotides in their genome. Techniques are available to do this, but those techniques typically take many days and thousands upon thousands of dollars to perform. Furthermore, clinical relevance of any individual's genomic sequence is a matter of comparing unique features of their genomic sequence (i.e. their genotype) to reference genomes that are correlated with known characteristics (i.e. phenotypes). The issue of scale and throughput becomes evident when one considers that the reference genomes are created based on correlations of genotype to phenotype that arise from research studies that typically use thousands of individuals in order to be statistically valid. Thus, billions of nucleotides can eventually be sequenced for thousands of individuals to identify any clinically relevant genotype to phenotype correlation. Multiplied further by the number of diseases, drug responses, and other clinically relevant characteristics, the need for very inexpensive and rapid sequencing technologies becomes ever more apparent.

What is needed is a reduction in the cost of sequencing that drives large genetic correlation studies carried out by research scientists and that makes sequencing accessible in the clinical environment for the treatment of individual patients making life changing decisions. Embodiments of the invention set forth herein satisfy this need and provide other advantages as well.

BRIEF SUMMARY

The present disclosure provides a detection apparatus that includes (a) a carriage including a plurality of microfluorometers, wherein each of the microfluorometers has an objective configured for wide-field image detection, wherein the plurality of microfluorometers is positioned to simultaneously acquire a plurality of the wide-field images in a common plane, and wherein each of the wide-field images is from a different area of the common plane; (b) a translation stage configured to move the carriage in at least one direction parallel to the common plane; and (c) a sample stage configured to hold a substrate in the common plane.

This disclosure further provides a method of imaging a substrate, including the steps of (a) providing a substrate including fluorescent features on a surface; (b) acquiring a plurality of wide-field images of a first portion of the surface using a plurality of microfluorometers, wherein each of the microfluorometers acquires a wide-field image from a different location of the surface, wherein the plurality of microfluorometers are affixed to a carriage; and (c) translating the carriage in a direction parallel to the surface and repeating (b) for a second portion of the surface. The method can use any of the apparatus set forth elsewhere herein, but need not be so limited in all embodiments.

Also provided is a fluidics cartridge that includes (a) a flow cell having an optically transparent surface, an inlet and an outlet; and (b) a housing made of a material that is optically opaque and impermeable to aqueous liquids, wherein the housing holds: (i) a sample reservoir; (ii) a fluidic line between the sample reservoir and the inlet of the flow cell; (iii) a plurality of reagent reservoirs in fluid communication with the flow cell via the inlet of the flow cell, (iv) at least one valve configured to mediate fluid communication between the reservoirs and the inlet of the flow cell; and (v) at least one pressure source configured to move liquids from the sample reservoir or the reagent reservoirs to the flow cell via the inlet of the flow cell, wherein an optically transparent window interrupts the housing and an inlet port interrupts the housing, wherein the inlet port is in fluid communication with the sample reservoir, and wherein the optically transparent surface is positioned in the window.

This disclosure further provides a sequencing method that includes the steps of (a) providing a fluidic cartridge having (i) a flow cell having an optically transparent surface, (ii) a nucleic acid sample, (iii) a plurality of reagents for a sequencing reaction, and (iv) a fluidic system for delivering the reagents to the flow cell; (b) providing a detection apparatus having (i) a plurality of microfluorometers, wherein each of the microfluorometers comprises an objective configured for wide-field image detection in an image plane in x and y dimensions, and (ii) a sample stage; (c) delivering the fluidic cartridge to the sample stage, wherein the optically transparent surface is placed in the image plane; and (d) carrying out fluidic operations of a nucleic acid sequencing procedure in the fluidic cartridge and detection operations of the nucleic acid sequencing procedure in the detection apparatus, wherein (i) the reagents are delivered to the flow cell by the fluidic system, and (ii) the nucleic acid features are detected by the plurality of microfluorometers.

DETAILED DESCRIPTION

Figure 1:
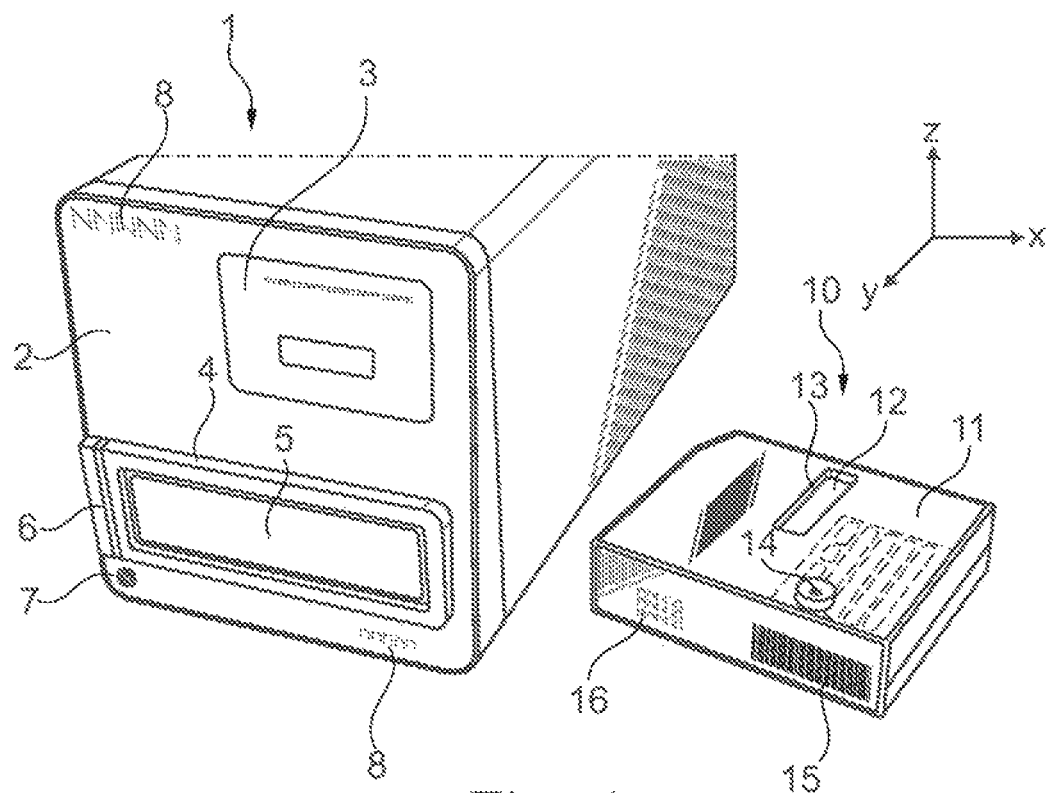
FIG. 1 shows an optoelectronic detection device (left) and a fluidic cartridge (right) useful for nucleic acid sequencing.

This disclosure provides methods and apparatus for high-resolution detection of planar areas such as those present on substrate surfaces. A particularly useful application is optically based imaging of a biological sample that is present on a surface. For example, the methods and apparatus set forth herein can be used to obtain images of nucleic acid features that are present in nucleic acid arrays, such as those used in nucleic acid sequencing applications. A variety of nucleic acid sequencing techniques that utilize optically detectable samples and/or reagents can be used. These techniques are particularly well suited to the methods and apparatus of the present disclosure and therefore highlight various advantages for particular embodiments of the invention. Some of those advantages are set forth below for purposes of illustration and, although nucleic acid sequencing applications are exemplified, the advantages can be extended to other applications as well.

In regard to some of the examples set forth herein, salient characteristics of many nucleic acid sequencing techniques are (1) the use of multicolor detection (e.g. often four different fluorophores are used, one for each of the different nucleotide types A, C, G and T (or U) present in nucleic acids), (2) distribution of large numbers of different fragments from a nucleic acid sample (e.g. fragments from a genome sample, RNA sample, or derivative thereof) onto the surface of an array and (3) repeated cycles of fluidic processing and imaging of the arrays. Embodiments of the methods and apparatus disclosed herein are particularly useful for nucleic acid sequencing because they can provide the capability of high resolution imaging of array surfaces in multiple colors and in multiple repetitions. For example, embodiments set forth herein allow an image of a surface to be obtained at a resolution that is in the range of hundreds, tens or even single digit microns. As such, nucleic acid features having nearest neighbor, average center-to-center spacing that is lower than 100 microns, 50 microns, 10 microns, 5 micron or fewer can be resolved. In particular embodiments, wide-field images of surfaces can be acquired, including for example, images that cover an area of 1 $mm^2$ or more of an array. The images can be acquired in multiple colors simultaneously or sequentially, for example, to identify fluorescent labels uniquely associated with different nucleotide types. Moreover, images can be acquired sequentially for multiple cycles of a sequencing technique. The images from a given area of the array can be reliably compared from each cycle to determine the sequence of color changes detected for each nucleic acid feature on the array. The sequence of color changes can in turn be used to infer the sequences of the nucleic acid fragments in each feature.

In particular embodiments, an apparatus of the present disclosure includes one or more microfluorometers. Each of the microfluorometers can include an excitation radiation source, a detector and an objective to form an integrated subunit of a read head. Other optical components can be present in each microfluorometer. For example a beam splitter can be present to provide for a compact epifluorescent detection configuration, whereby the beam splitter is positioned to direct excitation radiation from the excitation radiation source to the objective and to direct emission radiation from the objective to the detector.

An advantage of using an integrated microfluorometer design is that the microfluorometer can be conveniently moved, for example in a scanning operation, to allow imaging of a substrate that is larger than the field of view of the microfluorometer. In particular embodiments, several microfluorometers can be combined to form a read head. Various configurations for the combination of read heads are set forth below and can be selected to suit a particular format for a substrate that is to be imaged, while maintaining relatively compact size for the overall read head. The relatively small size and low mass of the read head in several embodiments of the present disclosure results in relatively low inertia such that the read head comes to rest quickly after being moved, thereby favoring rapid scanning of a nucleic acid array or other substrate. In some cases, the microfluorometers can be affixed to a carriage such that they are not independently moveable in at least some dimensions during the course of an analytical application such as a nucleic acid sequencing run. For example, multiple microfluorometers can be permanently fixed such that they are not independently moveable with respect to each other in x and y dimensions (where at least one of x or y is the direction of scan). The microfluorometers may, however, be independently actuated in the z dimension to provide for independent focus control. Reducing degrees of freedom between several different microfluorometers of an apparatus of the present disclosure provides for protection against loss of alignment during shipping, handling and use of the apparatus.

In some embodiments, multiple microfluorometers that are present in a read head or carriage can each have a dedicated autofocus module. Accordingly, each microfluorometer can be independently focused. In some embodiments, a particular autofocus modules in a read head, although dedicated to actuation of a particular microfluorometer, can nevertheless receive information from at least one other autofocus module in the read head and the information from that particular autofocus module and from the at least one other autofocus module can be used to determine an appropriate actuation to achieve desired focus for the particular microfluorometer. In this way focus for any given microfluorometer can be determined by consensus between two or more microfluorometers present in the same read head or carriage.

In particular embodiments, a sample that is to be detected in a method or apparatus set forth herein can be provided in a cartridge format. For example, the cartridge can include a substrate to be detected along with other fluidic components used to process the substrate for detection. Taking the more specific example of a nucleic acid sequencing application, the cartridge can include a flow cell capable of presenting an array of nucleic acid features to a detection device, and optionally one or more of reservoirs for holding sequencing reagents, reservoirs for holding sample preparation reagents, reservoirs for holding waste products generated during sequencing, and/or pumps, valves and other components capable of moving fluids through the flow cell. A fluidic cartridge as such can provide the advantages of a convenient and compact format for storage and processing of a sample and reagents for nucleic acid sequencing.

In particular embodiments a fluidic cartridge can be configured to allow re-use of one or more reagents. For example, the fluidic cartridge can be configured to deliver a reagent to a flow cell, then remove the reagent from the flow cell, and then re-introduce the reagent to the flow cell. An advantage of re-using reagents is to reduce waste and reduce the cost of processes that utilize expensive reagents and/or reagents that are delivered at high concentrations (or in high amounts).

Fluidic cartridges of the present disclosure can provide an advantage of modularity whereby different samples can be fluidically processed in a first module (i.e. the fluidic cartridge) that is in optical communication with a second module (e.g. a microfluorometer, read head or detection apparatus). A fluidic cartridge can contain sample(s), reagents and fluidic hardware sufficient for an entire fluidic processing procedure (e.g. a nucleic acid sequencing procedure) and the fluidic cartridge can be delivered to a detection apparatus. Once the fluidic and detection procedures are complete, the fluidic cartridge can be removed such that the detection apparatus is ready for another procedure. Because the fluidic module and detection module are separable, the present system allows multiple different samples to be evaluated while avoiding the risk of cross contamination between samples. This provides advantages for embodiments where the detection components are relatively expensive and technically difficult to assemble, by avoiding unnecessary maintenance, decontamination or disposal of optical components that may be necessary when fluidic components and optical components are not modular.

FIG. 1 shows an exemplary optical scanning device 1 that exploits advantages of integrated optoelectronics and cartridge-based fluidics that are provided by several embodiments set forth herein. The exemplary device 1 includes a housing 2 that contains various fixed components including, for example, optical components, computational components, power source, fan and the like. A screen 3 present, for example, on the front face of the housing 2 functions as a graphical user interface that can provide various types of information such as operational status, status of an analytical procedure (e.g. a sequencing run) being carried out, status of data transfer to or from the device 1, instructions for use, warnings or the like. A cartridge receptacle 4 is also present on the front face of the housing 2. As shown, the cartridge receptacle 4 can be configured as a slot having a protective door 5. A status indicator 6, in the form of an indicator light on the frame of the cartridge receptacle in this example, is present and can be configured to indicate the presence or absence of a cartridge in the device 1. For example the indicator light 6 can change from on to off or from one color to another to indicate presence or absence of a cartridge. A power control button 7 is present on the front face of the housing 2 in this example as is identifying indicia 8 such as the name of the manufacturer or instrument.

Also shown in FIG. 1 is an exemplary fluidic cartridge 10 that can be used to provide a sample and reagents to the device 1. The fluidic cartridge 10 includes a housing 11 that protects various fluidic components such as reservoirs, fluidic connections, pumps, valves and the like. A flow cell 12 is integrated into the fluidic cartridge in a position where it is in fluid communication with reagents within the housing. The housing 11 has an opening 13 through which a face of the flow cell 12 is exposed such that it can interact optically with the optical scanning device 1 when the fluidic cartridge 10 is placed in the cartridge receptacle 4. The cartridge housing 11 also includes a sample port 14 for introduction of a target nucleic acid sample. A bar code 15 or other machine readable indicia can optionally be present on the cartridge housing 11, for example, to provide sample tracking and management. Other indicia 16 can also be present on the housing for convenient identification by a human user, for example, to identify the manufacturer, analytical analysis supported by the fluidic cartridge, lot number, expiration date, safety warnings and the like.

The apparatus shown in FIG. 1 is exemplary. Further exemplary embodiments of the methods and apparatus of the present disclosure that can be used alternatively or additionally to the example of FIG. 1 are set forth in further detail below.

Provided herein is a detection apparatus, having (a) a carriage including a plurality of microfluorometers, wherein each of the microfluorometers includes an objective configured for wide-field image detection, wherein the plurality of microfluorometers is positioned to simultaneously acquire a plurality of the wide-field images in a common plane, and wherein each of the wide-field images is from a different area of the common plane; (b) a translation stage configured to move the carriage in at least one direction parallel to the common plane; and (c) a sample stage configured to hold a substrate in the common plane.

A detection apparatus (or an individual microfluorometer) of the present disclosure can be used to obtain one or more images at a resolution that is sufficient to distinguish features on a micron scale. For example, a microfluorometer that is used in a detection apparatus can have a resolution that is sufficient to distinguish features that are separated by at most 500 µm, 100 µm, 50 µm, 10 µm, 5 µm, 4 µm, 3 µm, 2 µm or 1 µm. Lower resolution is also possible, for example, a resolution that distinguishes features that are separated by more than 500 µm.

A detection apparatus (or an individual microfluorometer) of the present disclosure is well suited for high-resolution detection of surfaces. Accordingly, arrays having features with average spacing in the micron range are especially useful substrates. In particular embodiments, a detection apparatus or microfluorometer can be used to obtain one or more images of an array having features with center-to-center spacing for nearest neighbors that is on average at or below 500 µm, 100 µm, 50 µm, 10 µm, 5 µm, 4 µm, 3 µm, 2 µm or 1 µm. In many embodiments the features of an array are non-contiguous being separated, for example, by less than 100 µm, 50 µm, 10 µm, 5 µm, 1 µm, or 0.5 µm. However, the features need not be separated. Instead some or all of the features of an array can be contiguous with each other.

Any of a variety of arrays (also referred to as "microarrays") known in the art can be used. A typical array contains features, each having an individual probe or a population of probes. In the latter case, the population of probes at each site is typically homogenous having a single species of probe. For example, in the case of a nucleic acid array, each feature can have multiple nucleic acid species each having a common sequence. However, in some embodiments the populations at each feature of an array can be heterogeneous. Similarly, protein arrays can have features with a single protein or a population of proteins typically, but not always, having the same amino acid sequence. The probes can be attached to the surface of an array for example, via covalent linkage of the probes to the surface or via non-covalent interaction(s) of the probes with the surface. In some embodiments, probes, such as nucleic acid molecules, can be attached to a surface via a gel layer as described, for example, in US 2011/0059865 A1, which is incorporated herein by reference.

Exemplary arrays include, without limitation, a BeadChip Array available from ILLUMINA®, Inc. (San Diego, Calif.) or others such as those where probes are attached to beads that are present on a surface (e.g. beads in wells on a surface) such as those described in U.S. Pat. Nos. 6,266,459; 6,355, 431; 6,770,441; 6,859,570; or 7,622,294; or PCT Publication No. WO 00/63437, each of which is incorporated herein by reference. Further examples of commercially available micro arrays that can be used include, for example, an AFFYMETRIX® GENECHIP® micro array or other microarray synthesized in accordance with techniques sometimes referred to as VLSIPS™ (Very Large Scale Immobilized Polymer Synthesis) technologies. A spotted micro array can also be used in an apparatus or system according to some embodiments of the invention. An exemplary spotted micro array is a CODELINK™ Array available from Amersham Biosciences. Another microarray that is useful is one that is manufactured using inkjet printing methods such as SUREPRINT™ Technology available from Agilent Technologies.

Other useful arrays include those that are used in nucleic acid sequencing applications. For example, arrays having amplicons of genomic fragments (often referred to as clusters) are particularly useful such as those described in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, or US 2008/0108082, each of which is incorporated herein by reference. Another type of array that is useful for nucleic acid sequencing is an array of particles produced from an emulsion PCR technique. Examples are described in Dressman et al., *Proc. Natl. Acad. Sci. USA* 100:8817-8822 (2003), WO 05/010145, US 2005/0130173 or US 2005/ 0064460, each of which is incorporated herein by reference in its entirety. Although the above arrays have been described in the context of sequencing applications, it will be understood that the arrays can be used in other embodiments including, for example, those that do not include a sequencing technique.

Whether configured for detection of an array or other sample, one or more microfluorometers that are present in a detection apparatus can be configured for wide-field detection. The field diameter for an individual microfluorometer can be, for example, at least 0.5 mm, 1 mm, 2 mm, 3 mm, 4 mm, 5 mm or larger. By choice of appropriate optical components the field diameter can be limited to a maximum area as well and, as such the field diameter can be, for example, no larger than 5 mm, 4 mm, 3 mm, 2 mm or 1 mm. Accordingly, in some embodiments an image obtained by an individual microfluorometer can have an area that is in a range of 0.25 mm$^2$ to 25 mm$^2$.

In addition to being configured for wide-field detection, a microfluorometer can be configured to have a numerical aperture (NA) that is greater than 0.2. For example, the NA of an objective used in a microfluorometer of the present disclosure can be at least 0.2, 0.3, 0.4, or 0.5. Alternatively or additionally, it may be desirable to restrict the NA of the objective to be no greater than 0.8, 0.7, 0.6 or 0.5. The methods and apparatus set forth herein are particularly useful when detection occurs through an objective having a NA between 0.2 and 0.5.

In array detection embodiments, a detection apparatus (or individual microfluorometer) can be configured to obtain a digital image of the array. Typically, each pixel of the digital detection apparatus (or individual microfluorometer) will collect signal from no more than a single feature in any given image acquisition. This configuration minimizes unwanted 'cross talk' between features in the image. The number of pixels that detect signal from each feature can be adjusted based on the size and shape of the features imaged and based on the configuration of the digital detection apparatus (or individual microfluorometer). For example, each feature can be detected in a given image by no more than about 16 pixels, 9 pixels, 4 pixels, or 1 pixel. In particular embodiments, each image can utilize on average 6.5 pixels per feature, 4.7 pixels per feature or 1 pixel per feature. The number of pixels used per feature can be reduced, for example, by reducing variability in the position of features in the pattern of the array and tightening the tolerance for alignment of the detection apparatus to the array. Taking as an example a digital detector that is configured to use fewer than 4 pixels per feature, image quality can be improved by using an array of ordered nucleic acid features in place of an array of randomly distributed nucleic acid clusters.

It will be understood that a detection apparatus having multiple microfluorometers can detect an area of a common plane that is roughly equivalent to the number of microfluorometers multiplied by the wide-field area detected by each microfluorometer. The areas need not be contiguous. For example, 2 or more microfluorometers can be positioned to detect discrete regions of a common plane that are separated by an undetected area. However, if desired, multiple microfluorometers can be positioned to detect areas that are contiguous, but not overlapping. In alternative embodiments a detection apparatus having multiple microfluorometers can detect an area of a common plane that is substantially less than the number of microfluorometers multiplied by the wide-field area detected by each microfluorometer. This can result, for example, when multiple microfluorometers are positioned to detect areas that have at least a partial overlap. As set forth in further detail elsewhere herein, multiple images need not be acquired in a format that is used for or that even supports reconstruction of a complete image of an array or other common plane that has been detected.

Figure 2:
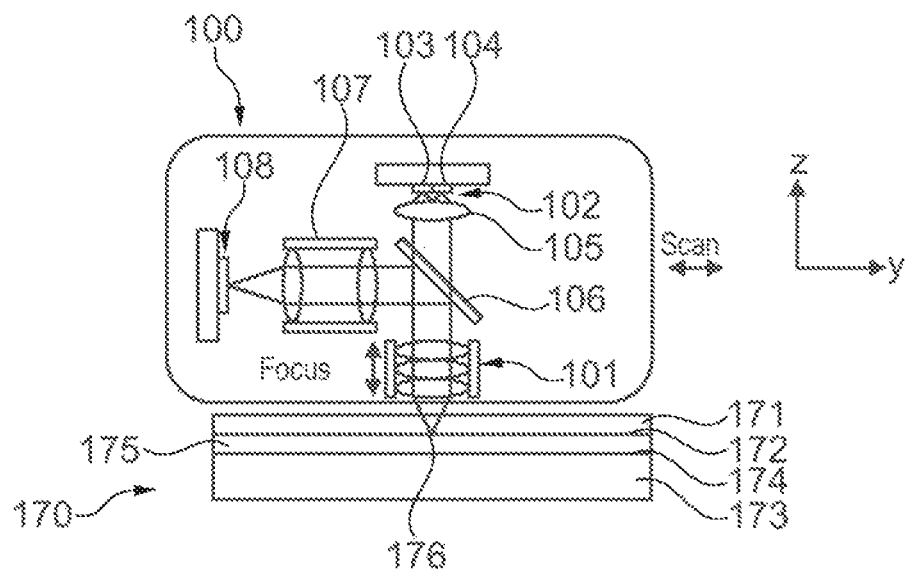
FIG. 2 shows an optical layout for an individual microfluorometer having orthogonal excitation and emission beam paths.

An exemplary optical layout for a microfluorometer 100 is shown in FIG. 2. The microfluorometer 100 is directed to a flow cell 170 having an upper layer 171 and a lower layer 173 that are separated by a fluid filled channel 175. In the configuration shown, the upper layer 171 is optically transparent and the microfluorometer 100 is focused to an area 176 on the inner surface 172 of the upper layer 171. In an alternative configuration the microfluorometer 100 can be focused on the inner surface 174 of the lower layer 173. One or both of the surfaces can include array features that are to be detected by the microfluorometer 100.

The microfluorometer 100 includes an objective 101 that is configured to direct excitation radiation from a radiation source 102 to the flow cell 170 and to direct emission from the flow cell 170 to a detector 108. In the exemplary layout, excitation radiation from the radiation source 102 passes through a lens 105 then though a beam splitter 106 and then through the objective on its way to the flow cell 170. In the embodiment shown the radiation source includes two light emitting diodes (LEDs) 103 and 104, which produce radiation at different wavelengths from each other. The emission radiation from the flow cell 170 is captured by the objective 101 and is reflected by the beam splitter through conditioning optics 107 and to the detector 108 (e.g. a CMOS sensor). The beam splitter 106 functions to direct the emission radiation in a direction that is orthogonal to the path of the excitation radiation. The position of the objective can be moved in the z dimension to alter focus of the microfluorometer. The microfluorometer 100 can be moved back and forth in the y direction to capture images of several areas of the inner surface 172 of the upper layer 171 of the flow cell 170.

Figure 3:
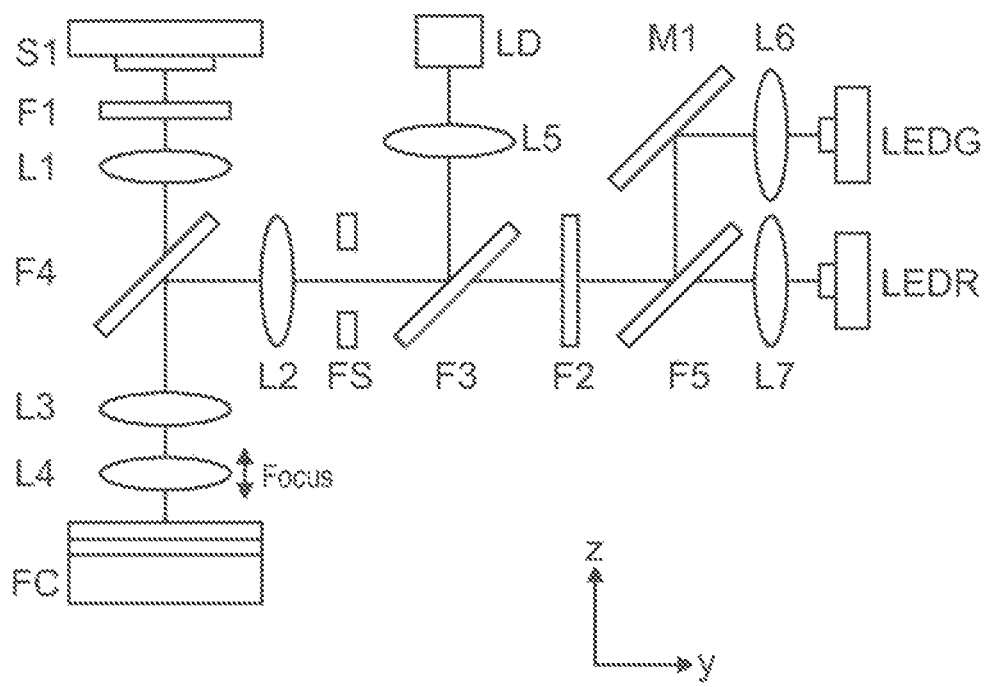
FIG. 3 shows an optical layout for a microfluorometer.

FIG. 3 shows an exploded view of an exemplary microfluorometer for purposes of demonstrating functional arrangement for various optical components. Two excitation sources are shown, including a green LED (LEDG) and a red LED (LEDR). Excitation light from each passes through a green LED collector lens (L6) and red LED collector lens (L7), respectively. An LED fold mirror (M1) reflects the green excitation radiation to a combiner dichroic (F5) which reflects the green excitation radiation through an excitation filter (F2), then through a laser diode beam splitter (F3), then through an excitation field stop (FS), then through an excitation projection lens group L2 to an excitation/emission dichroic (F4) which reflects the green excitation radiation through a stationary objective lens group (L3) and a translating objective lens group (L4) to the surface of a flow cell (FC). The red excitation radiation passes from the red LED collector lens (L7) to the combiner dichroic (F5) after which the red excitation radiation follows the same path as the green excitation radiation to the surface of the flow cell (FC). As shown in the figure, focusing is actuated by moving the translating objective lens group (L4) up and down (i.e. along the z dimension). Emission from the flow cell (FC) surface passes back through the translating objective lens group (L4), and then through the stationary objective lens group (L3) to the excitation/emission dichroic (F4) which passes the emission radiation to the emission projection less group (L1) through to the emission filter and then to the CMOS image sensor (S1). A laser diode (LD) is also directed via a laser diode coupling lens group (L5) to the laser diode beam splitter (F3) which reflects the laser diode radiation through the excitation field stop (FS), the excitation projection lens group (L2), the excitation/emission dichroic (F4), the stationary objective lens group (L3) and the translating objective lens group (L4) to the flow cell (FC).

As demonstrated by the exemplary embodiments of FIG. 2 and FIG. 3, each of the microfluorometers can include a beam splitter and a detector, wherein the beam splitter is positioned to direct excitation radiation from an excitation radiation source to the objective and to direct emission radiation from the objective to the detector. As shown in the figures, each microfluorometer can optionally include an excitation radiation source such as an LED. In this case, each microfluorometer can include a dedicated radiation source, such that the read head includes several radiation sources each separated into individual microfluorometers. In some embodiments, two or more microfluorometers can receive excitation radiation from a common radiation source. As such the two or more microfluorometers can share a radiation source. In an exemplary configuration, a single radiation source can direct radiation to a beam splitter that is positioned to separate the excitation radiation into two or more beams and directs the beams to two or more respective microfluorometers. Additionally or alternatively, excitation radiation can be directed from a radiation source to one, two or more microfluorometers via one or more optical fibers.

It will be understood that the particular components shown in the figures are exemplary and can be replaced with components of similar function. For example, any of a variety of radiation sources can be used instead of an LED. Particularly useful radiation sources are arc lamps, lasers, semiconductor light sources (SLSs), or laser diodes. LEDs can be purchased, for example, from Luminus (Billerica, Mass.). Similarly, a variety of detectors are useful including, but not limited to a charge-coupled device (CCD) sensor; photomultiplier tubes (PMT's); or complementary metal-oxide-semiconductor (CMOS) sensor. A particularly useful detector is a 5-megapixel CMOS sensor (MT9P031) available from Aptina Imaging (San Jose, Calif.).

FIG. 2 and FIG. 3 provide exemplary embodiments of a microfluorometer that includes two excitation sources. This configuration is useful for detecting at least two fluorophores that are excited at different wavelengths, respectively. If desired, a microfluorometer can be configured to include more than two excitation sources. For example, a microfluorometer can include at least 2, 3, 4 or more different excitation sources (i.e. sources producing different wavelengths from each other). Alternatively or additionally, beam splitters and optical filters can be used to expand the range of excitation wavelengths available from an individual radiation source. Similar use of multiple radiation sources and/or optical filtering of split excitation beams can be used for embodiments where several microfluorometers share excitation from one or more radiation sources. As set forth in further detail elsewhere herein, the availability of multiple excitation wavelengths is particularly useful for sequencing applications that utilize several different fluorophore labels.

Figure 4:
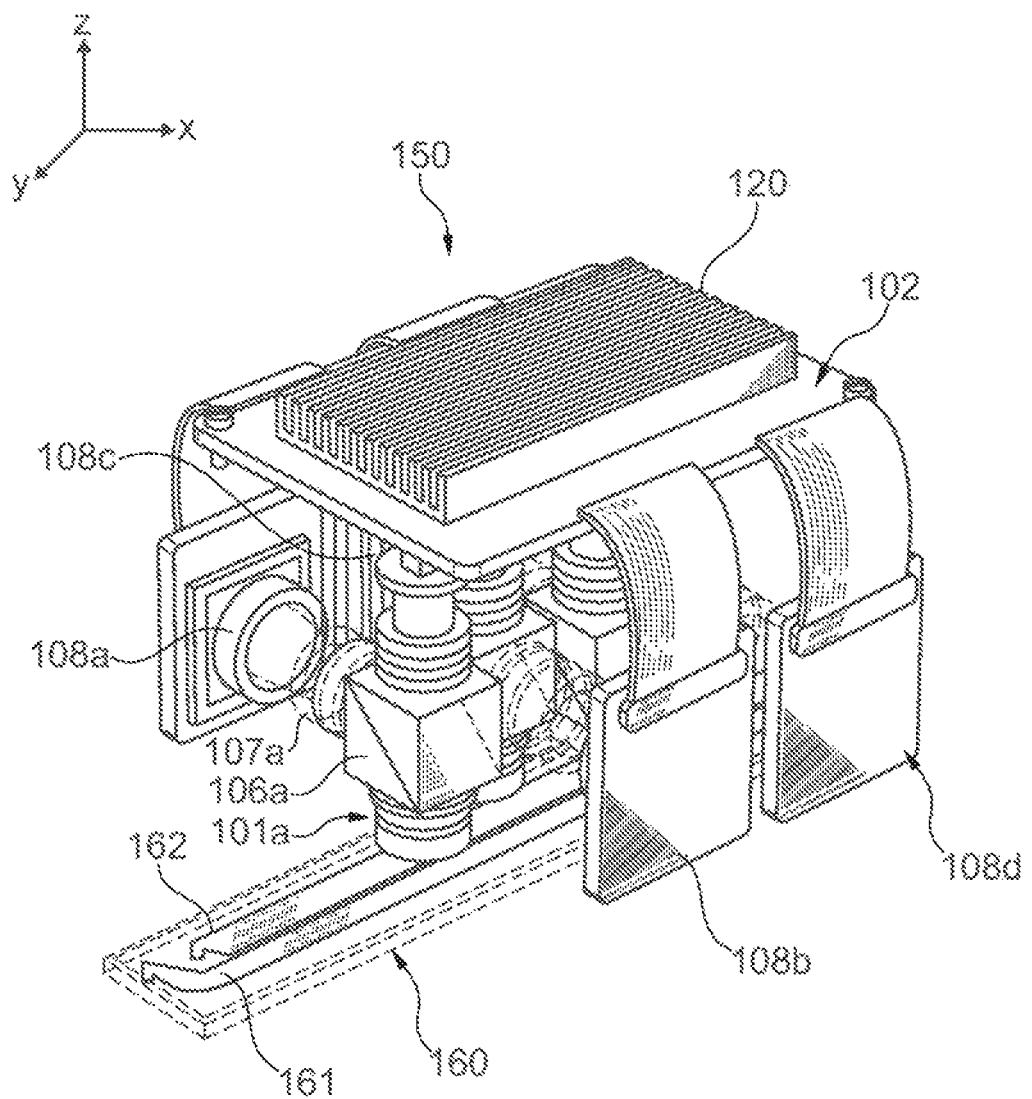
FIG. 4 shows an arrangement of four microfluorometers in relation to a flow cell having two channels.

FIG. 4 shows an exemplary arrangement of four microfluorometers in a single read head 150. The four microfluorometers are arranged in a staggered layout with respect to the channels 161 and 162 of a flow cell 160. In the arrangement shown, two of the microfluorometers (corresponding to detectors 108a and 108c) are configured to image separate regions of a first channel 161 and the other two microfluorometers (corresponding to detectors 108b and 108d) are configured to image separate regions of a second channel 162. As shown, the microfluorometers (corresponding to detectors 108*a* and 108*c*) are staggered with respect to the microfluorometers (corresponding to detectors 108*b* and 108*d*) in the x dimension such that the two pairs of microfluorometers can detect the adjacent channels 161 and 162 respectively. The microfluorometers each have an orthogonal emission and excitation path (as shown in FIG. 2) with the radiation sources 102 positioned on the same side of the read head, opposite the flow cell 160. Two of the detectors 108*a* and 108*c* are positioned on a first side of the read head and the other two detectors 108*b* and 108*d* are positioned on the opposite side, both sides being orthogonal to the side where the excitation sources are positioned. In the exemplary embodiment shown it FIG. 4 the four radiation sources are in thermal contact with a single large heat sink 120. A single large heat sink provides a greater degree of heat dissipation than many configurations that use an individual heat sink for each radiation source. However, if desired individual radiation sources can be thermally coupled to individual heat sinks (see, for example, FIG. 8 and related description below). An advantage of the arrangement of microfluorometers shown in FIG. 4 is the provision of a compact read head. Similar advantages can be derived for embodiments where the relative positions of the excitation source and detector in each microfluorometer are exchanged (see, for example, FIG. 8 and related description below).

The read head 150 shown in FIG. 4 is positioned to scan in the y dimension. The y dimension is parallel to the length of the flow cell 160 such that movement of the read head 150 in a scanning operation will result in imaging of areas along the length of the flow cell 160. The detectors 108*a*, 108*b*, 108*c* and 108*d* are positioned on opposite sides of the read head 150, and on opposing sides of the flow cell 160, the sides of the flow cell running along the scan direction. The orientation of the scan head 150 with respect to the flow cell 160 and scan direction is exemplary. Other orientations are also useful including for example, the orientation shown in FIG. 13 wherein the detectors are positioned on opposite sides of the read head but in a forward and backward position relative to the scan direction.

A microfluorometer, or read head having several microfluorometers, can be positioned above a flow cell (with respect to gravity's arrow) as exemplified for several embodiments set forth herein. However, it is also possible to position a microfluorometer, or a read head, underneath a flow cell. Accordingly a flow cell can be transparent on the top side, bottom side or both sides with respect to the wavelengths of excitation and emission radiation used. Indeed, in some embodiments it may be desirable to position microfluorometers on both sides of a flow cell or to position read heads on both sides of a flow cell. Other orientations with respect to gravity are also possible, including for example a side to side orientation between a flow cell and microfluorometer (or read head).

A microfluorometer or read head can be configured to detect the two opposing, inner surfaces of a flow cell from a single side of the flow cell. For example, the microfluorometer or read head can employ an optical compensator that is inserted and removed to detect alternative surfaces of the flow cell. Exemplary methods and apparatus for detecting opposing inner surfaces of a flow cell such as the use of optical compensators are described in U.S. Pat. No. 8,039,817, which is incorporated herein by reference in its entirety. A compensator is optional, for example, depending upon the NA and/or optical resolution of the apparatus.

Figure 5:
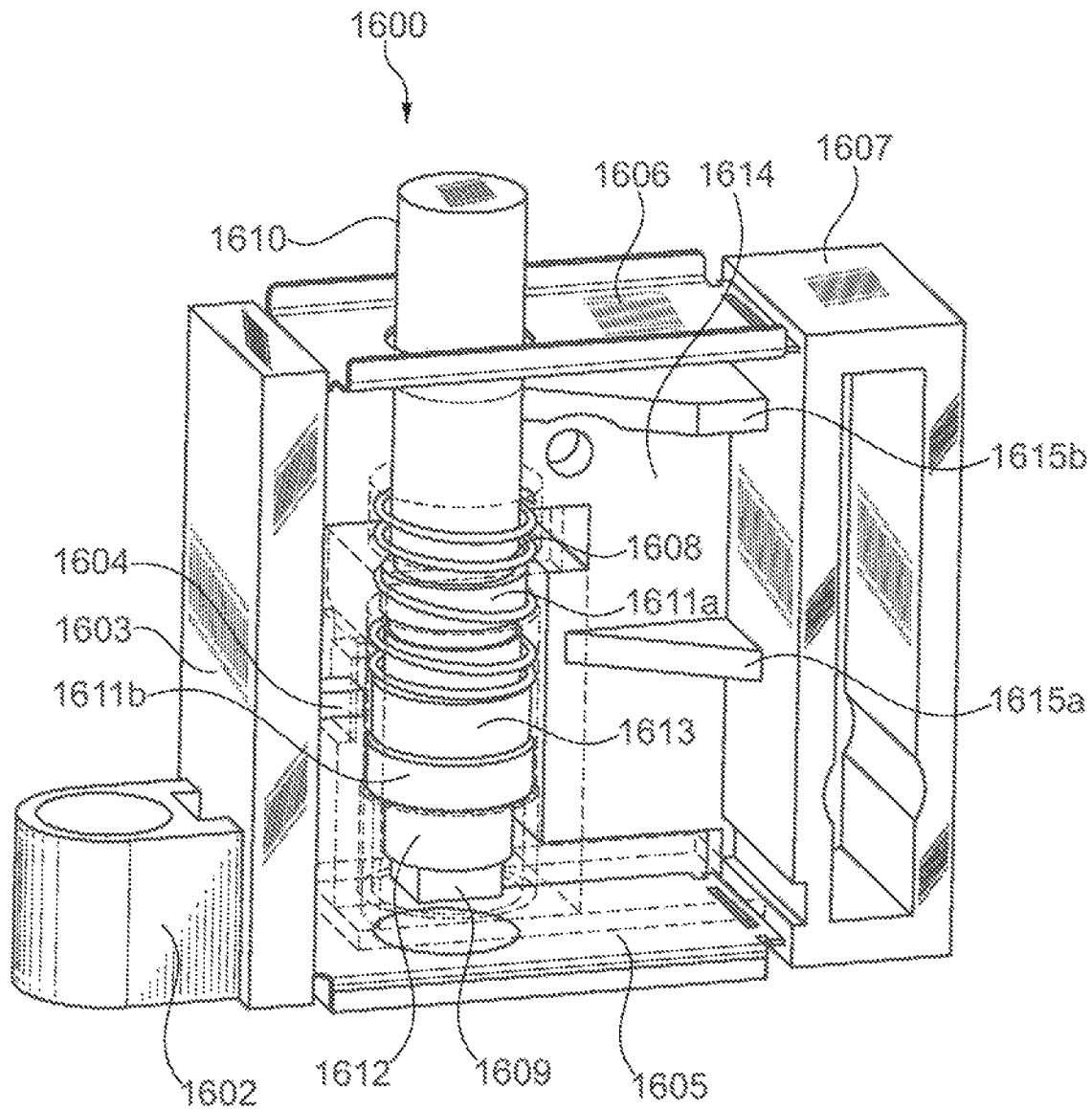
FIG. 5 shows an autofocus apparatus that can be used in a microfluorometer.

A microfluorometer used in an apparatus or method set forth herein can include an autofocus module. Accordingly, multiple microfluorometers that are present in a read head can each have a dedicated autofocus module. An exemplary autofocus module 1600 is shown in FIG. 5. The module includes a receptacle 1602 for an objective of a microfluorometer (for example, the translating objective lens shown in FIG. 3). The receptacle 1602 is affixed to a sliding support 1603 having a lever arm 1604. The lever arm 1604 interacts functionally with a motor 1610 that is configured to move the lever arm up and down (along the z direction). As such the motor 1610 actuates movement of the objective in the z direction to alter focus. The motor 1610 is a linear actuator using a lead screw. Rotation of an internal lead screw under rotational force of the motor causes lead nut 1613, through which the lead screw is threaded, to move up and down. Lead nut 1613 is positioned between two bearings 1611*a* and 1611*b*. Movement of the lead nut is biased against spring 1608. The lead nut 1613 is in physical contact with the lever arm 1604 such that the up and down movement of the lead nut actuates the up and down movement of the sliding support 1603 and consequently the objective. A sensor 1609 is located on the lower side of the autofocus module separated from the actuator by a spacer 1612.

The autofocus module 1600 shown in FIG. 5 further includes a structural support having a side body 1607 connected to a back plane 1614 and connected to a top flexure 1606 and a bottom flexure 1605. Rigidity can be provided by the box frame structure of the side body 1607. Further rigidity is provided by two triangle supports 1615*a* and 1615*b* between the side body 1607 and back plane 1614. The flexures 1606 and 1605 can be co-molded with the sliding support to provide high tolerance between sliding support 1603 and side body 1607.

As shown by the exemplary embodiment of FIG. 5, an autofocus module that is used in a microfluorometer can include a detector and an actuator, wherein the actuator is configured to alter the focus of the microfluorometer with respect to the common plane, and wherein the detector is configured to direct movement of the actuator. As such an autofocus module can include a dedicated detector that directs movement of the actuator. The dedicated detector can operate in a closed loop with the actuator without a need to communicate data outside of the microfluorometer or outside of the detection head in order to achieve automatic focusing. Alternatively or additionally, a detector outside of the autofocus module, such as the imaging detector that is used for wide-field imaging, can direct movement of the actuator. Thus, the same detector that is used for wide-field imaging and for outputting image data to a processing unit outside of the microfluorometer or read head can also be used to achieve automatic focusing.

In particular embodiments, autofocus modules for two or more microfluorometers in a read head can be configured to communicate with each other. For example, an autofocus module for a first microfluorometer of a read head can be configured to integrate data from an autofocus module for a second microfluorometer of the apparatus. In this way the autofocus module for the first microfluorometer can alter the focus of the first microfluorometer based on the perceived focus position of the first microfluorometer and the perceived focus position of the second microfluorometer. Thus, a detector for an autofocus module can be configured in a way that it is dedicated to focusing generally across a read head while not being configured for analytical image acquisition. Information from two different autofocus modules can be useful in determining tip-tilt of the read head.

Undesirable tip-tilt can be corrected by compensatory actuation of one or more microfluorometers based on the tip-tilt information.

Although automatic focusing has been exemplified with respect to a lead screw motor, it will be understood that autofocus modules using other actuation modalities can be used including for example, those that use a piezo motor or voice coil motor in place of the lead screw motor exemplified above.

Figure 6:
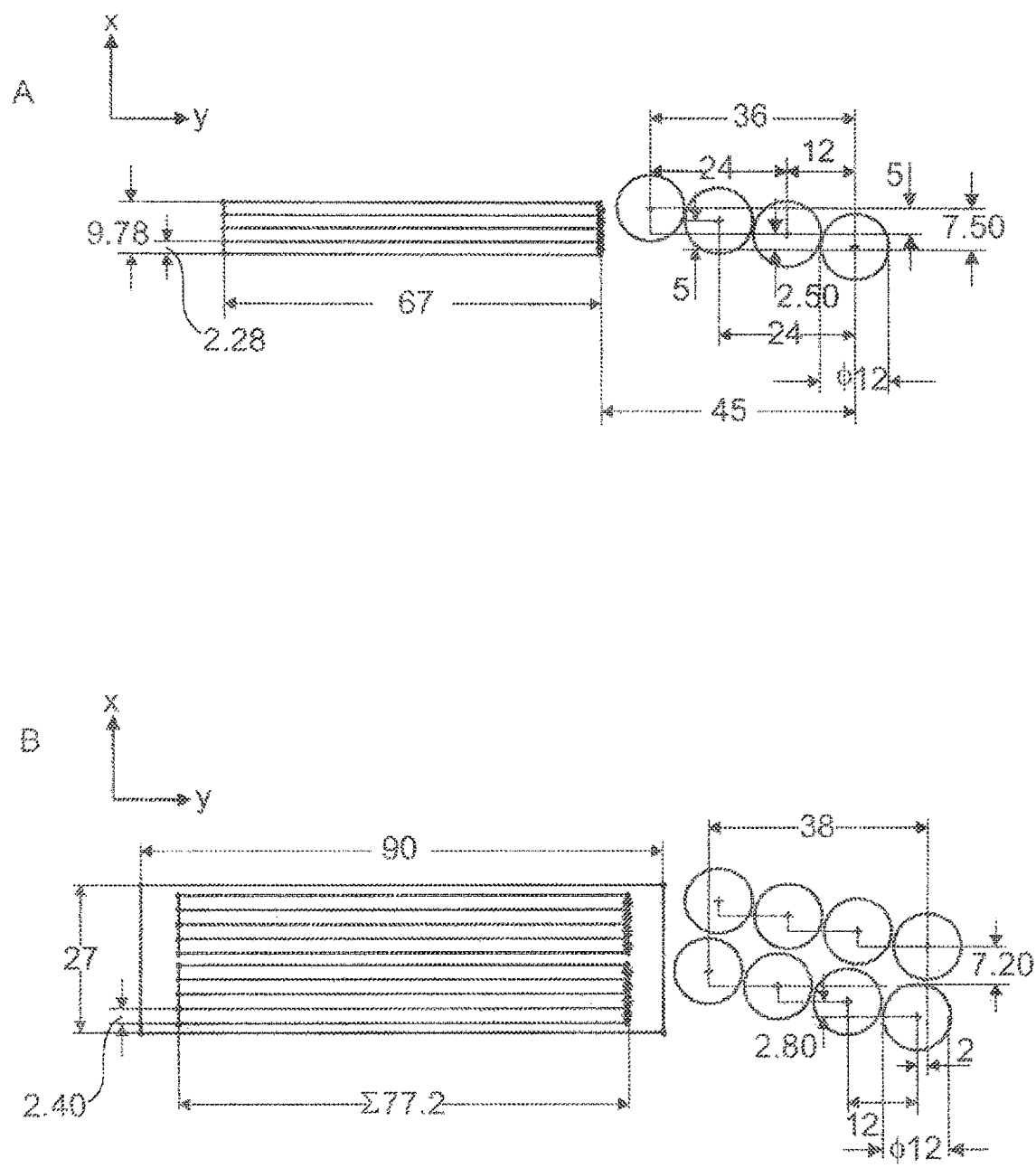
FIG. 6 shows in Panel A: top views of an arrangement of four channels in a flow cell (left) and a linear arrangement of objectives in a single row (right), and in Panel B: a flow cell having eight channels (left) and an arrangement of eight objectives in two linear rows of four.

A read head can include two or more microfluorometers, for example, attached to a carriage. For embodiments that utilize a multichannel flow cell, the read head can include a number of microfluorometers that correspond to the number of channels in the flow cell. As demonstrated previously by the example of FIG. 4, more than one microfluorometer per flow cell channel can be present. In particular embodiments, a read head can provide a single microfluorometer per flow channel. In the exemplary arrangement shown in FIG. 6, the flow cell has four channels and the read head has four microfluorometers. The figure shows a top plan view of the flow cell and objectives of the microfluorometers. For ease of demonstration components of the microfluorometers other than the objectives are not shown; however, those components can be positioned to achieve a compact design, for example, along the lines exemplified elsewhere herein. As shown in panel A of FIG. 6, the four objectives can be arranged in a linear relationship such that the objectives are closely packed and an imaginary straight line passes through the center point of each objective. The imaginary line can be offset at an angle with respect to the y dimension, the y dimension corresponding to the longest dimension of the flow cell (or direction of scan). The angle can be between 0° and 90° in the x-y quadrant and can be selected to accommodate the spacing of the channels in the flow cell (and the spacing of the objectives in the read head). FIG. 6A shows a relatively low angle of offset for a line passing through closely packed objectives which accommodates relatively closely packed channels. A higher angle of offset can be used to accommodate channels that are separated by greater distances from each other or objectives that are less closely packed.

Panel B of FIG. 6 shows an arrangement of multiple objectives in two lines. Here the flow cell includes eight channels and the read head has eight microfluorometers. The overall packing of the objectives in the two lines is approximately rectilinear. The arrangement accommodates closely packed objectives and two sets of closely packed channels (i.e. a first set of four closely packed channels and a second set of four closely packed channels). In this example, the two sets of closely packed channels are separated by a larger spacing than the spacing that separates individual channels in each set of four. It will be understood that the overall packing of the objectives in the two lines can be offset from rectilinear to accommodate different channel arrangements. Furthermore, as set forth in regard to a single line of objectives, the offset angle of the imaginary line running through the centers of both lines of objectives can be altered and/or the distance between objectives can be altered to accommodate different channel arrangements.

Figure 7:
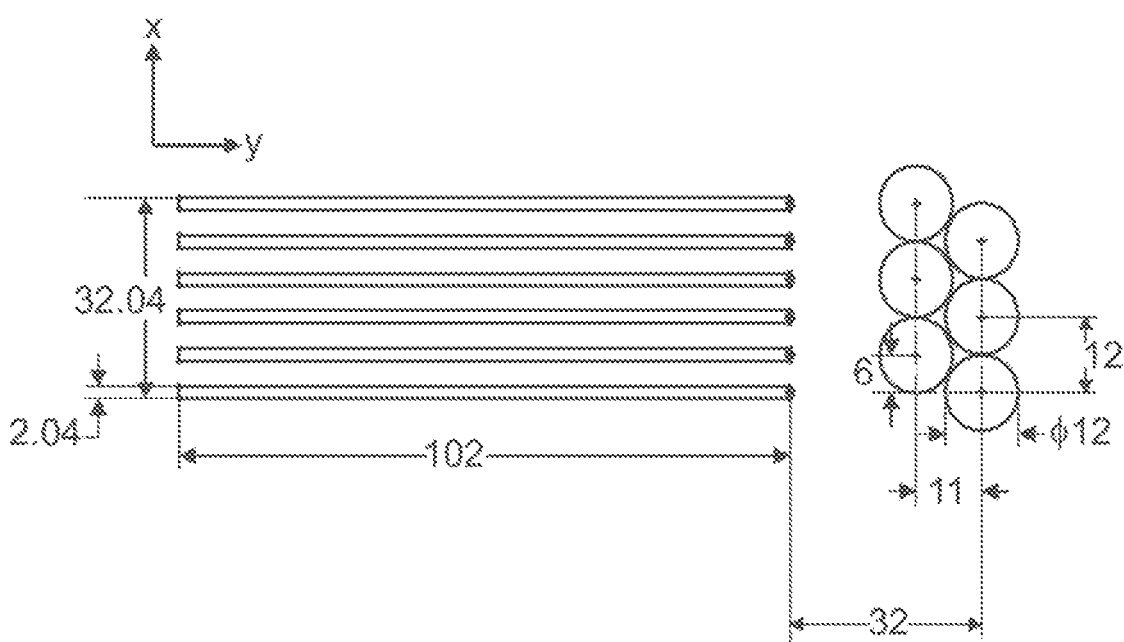
FIG. 7 shows top views of an arrangement of six channels in a flow cell (left) and a hexagonal packed arrangement of objectives in two rows (right).
Figure 8:
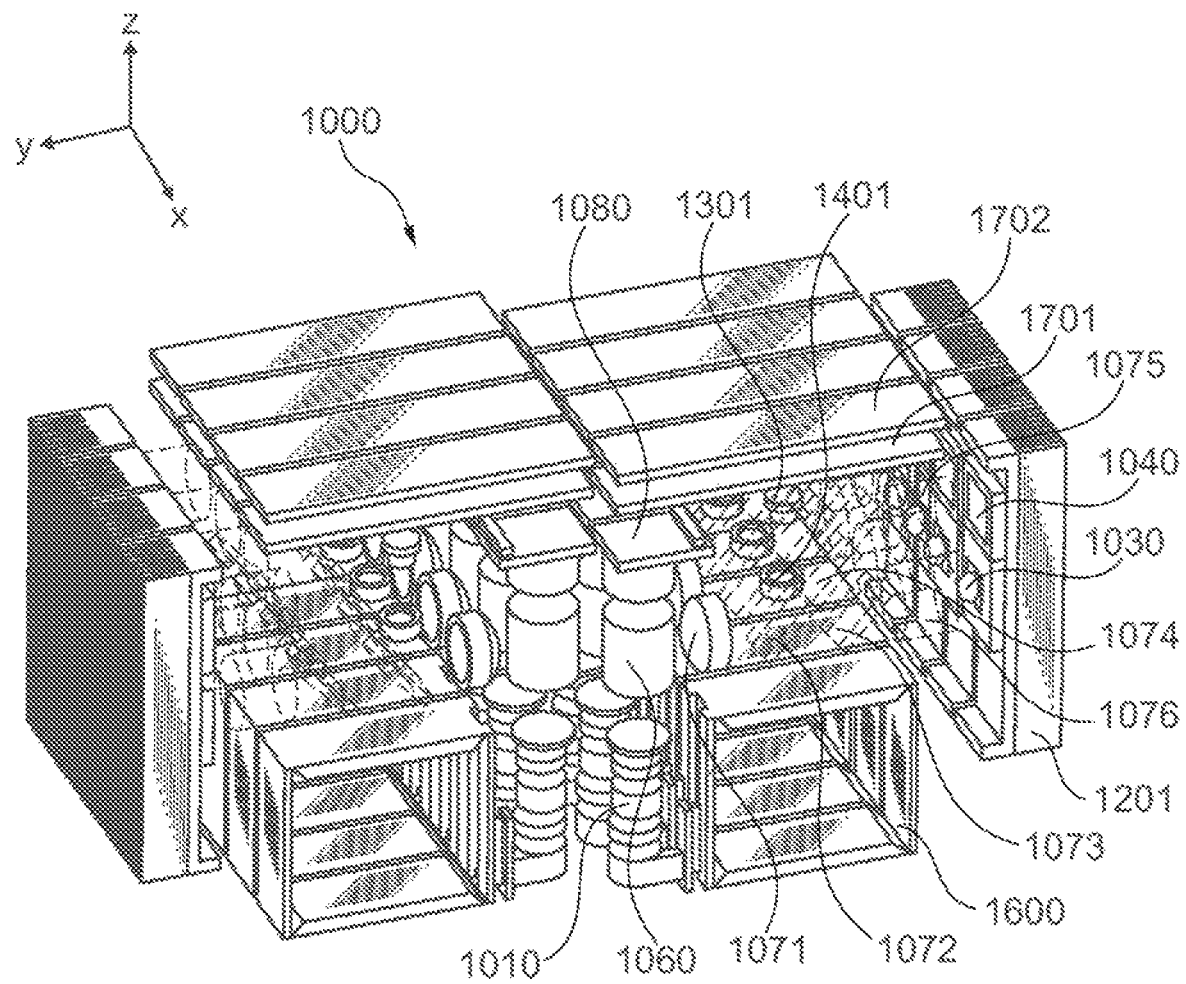
FIG. 8 shows a perspective view of an arrangement of eight microfluorometers for a detection apparatus.
Figure 9:
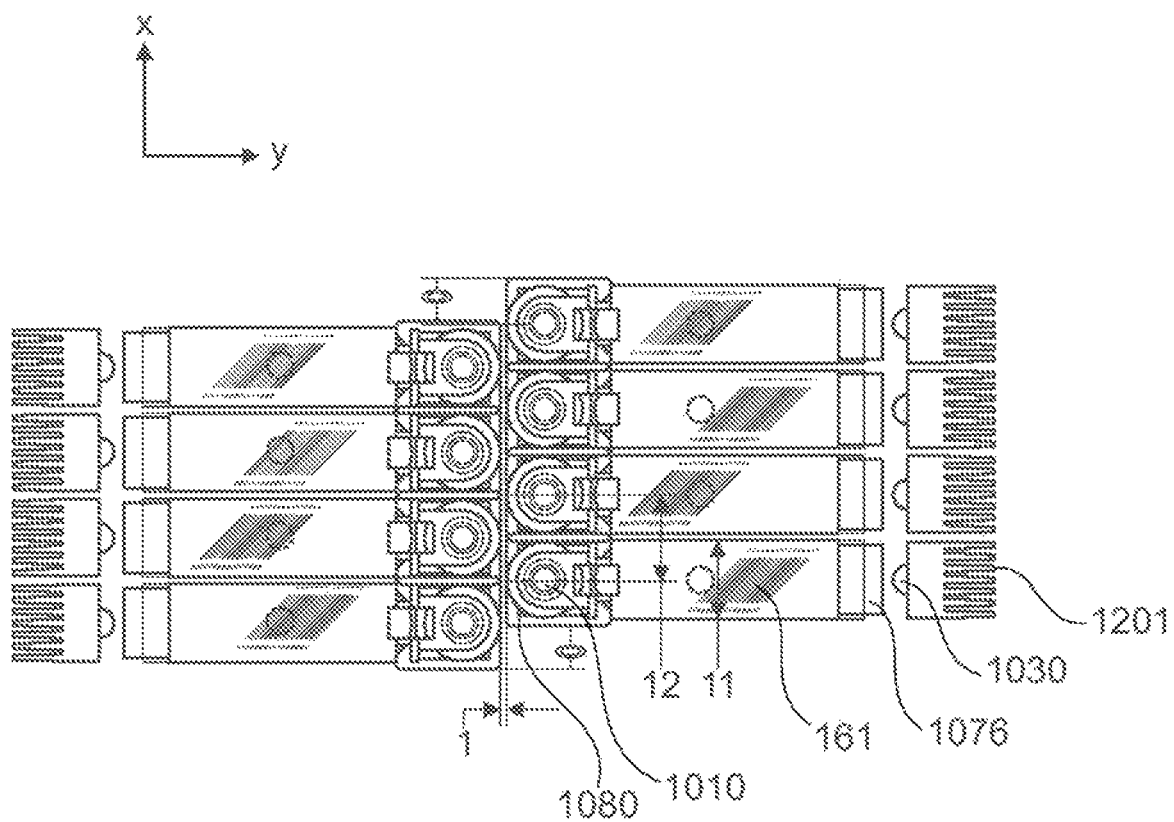
FIG. 9 shows a bottom plan view of an arrangement of eight microfluorometers for a detection apparatus.
Figure 13:
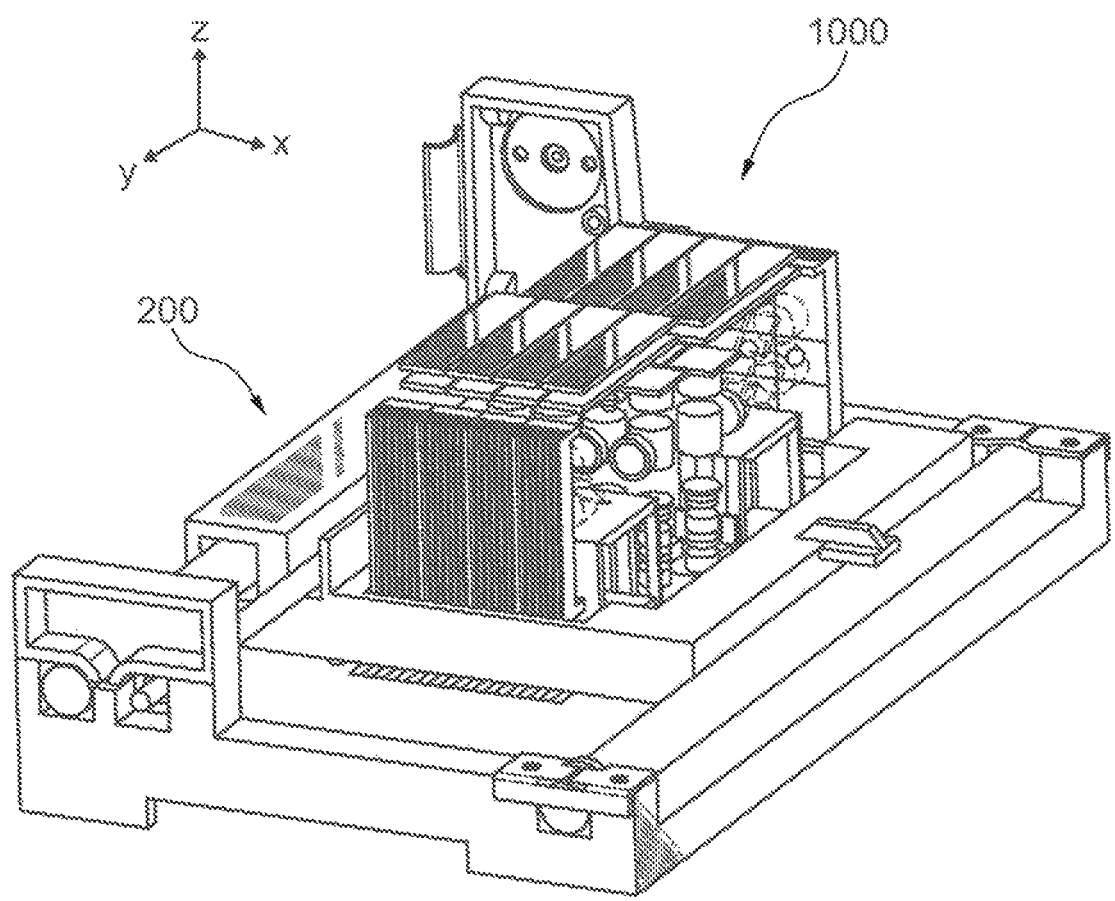
FIG. 13 shows a top perspective view of a Y-stage holding an arrangement of eight microfluorometers.

FIG. 7 demonstrates an arrangement of multiple objectives in which an imaginary line running through the centers of the objectives is at a 90° angle with respect to the longest dimension of the flow cell (or direction of scan). The imaginary line runs along the x axis. In this example, the objectives are in two rows and they are hexagonally packed. Hexagonal packing provides the advantage of maximum compaction in the x-y plane. The read head is shown with six objectives and the flow cell has six channels. It will be understood that similar arrangements can be used for a read head having only four objectives or for read heads having more than six objectives (e.g. eight objectives as shown in FIG. 8, FIG. 9, and FIG. 13). As evident by visual comparison, the flow cell channels are spaced further apart in the arrangement of FIG. 7 than in the arrangement of FIG. 6. However, the spacing of channels in both cases is within a useful and convenient range, for example, for nucleic acid sequencing applications.

As demonstrated by the examples of FIG. 6 and FIG. 7, each objective in a read head can be positioned to image at least a portion of an individual flow channel. Each objective can be positioned to image one and only one channel of a flow cell having several channels. An individual objective can be positioned to image a portion of one and only one channel, for example, when located at a particular y-stage position. Scanning in the y dimension can allow all or part of the channel to be imaged through the objective. In some cases, for example when the field diameter of the objective (or other limiting optical components of a microfluorometer) is less than the width of the channel, the objective can also be scanned in the x dimension to image all or part of the channel. Multiple objectives and their respective microfluorometers can be positioned such that several of the objectives are positioned to each obtain images for at least a portion of one and only one channel. Of course movement of a read head containing the multiple objectives and their respective microfluorometers can occur in the y and/or x direction to image all or part of each respective channel. These particular configurations are useful for multichannel flow cells as exemplified above. However, it will be understood that the configurations and underlying principles set forth above can be applied to an appropriate arrangement of several individual flow cells, each having only a single channel. Furthermore, as is the case generally for the methods and apparatus set forth herein, the arrangements can be applied to substrates other than flow cells.

A perspective view of a read head 1000 having an arrangement of eight microfluorometers is shown in FIG. 8. Each microfluorometer has a compact design similar to that shown in FIG. 3. For ease of demonstration the components of only one of the microfluorometers are labeled in FIG. 8 and will be described here. However, as visible in FIG. 8, each of the microfluorometers has similar components and configuration. Two excitation sources are present in each microfluorometer, including a green LED 1040 and a red LED 1030. Excitation light from the LEDs passes through a green LED collector lens 1075 and red LED collector lens 1076, respectively. An LED fold mirror 1074 reflects the green excitation radiation to a combiner dichroic 1073 which reflects the green excitation radiation through a laser diode beam splitter 1072, then through an excitation projection lens 1071 to an excitation/emission dichroic 1060 which reflects the green excitation radiation through an objective 1010. The red excitation radiation passes from the red LED collector lens 1076 to the combiner dichroic 1073 after which the red excitation radiation follows the same path as the green excitation radiation. The objective 1010 is positioned to collect emission radiation and direct it through excitation/emission dichroic 1060 which passes the emission radiation to the CMOS image sensor 1080. A laser diode 1301 is positioned to direct radiation via a laser diode coupling lens group 1401 to laser diode beam splitter 1072 which reflects the laser diode radiation through the excitation projection lens 1071, the excitation/emission dichroic 1060, and the objective 1010. An autofocus module 1600 is coupled to at least part of the objective 1010 and configured to translate the objective 1010 up and down (i.e. along the z dimension). The autofocus module can but need not include components of the autofocus apparatus exemplified in FIG. 5. It will be understood that additional optical components can be present in read head 1000 including, but not limited to those exemplified for Fig B. Furthermore, certain optical components can be absent from read head 1000 or modified in read head 1000 to suit particular applications. Printed circuit boards 1701 and 1702 can be configured to communicate with the detectors, autofocus modules and/or excitation sources.

FIG. 9 shows a bottom plan view of the read head 1000. Again for ease of demonstration, the components of only one of the microfluorometers are labeled in FIG. 9 and described herein. The red LED 1030 is shown in thermal communication with heat sink 1201 and in optical alignment with the red LED collector lens 1076. The green LED is obscured by the red LED 1030 and most of the excitation path is obscured by the autofocus module 1600 in this view. The objective 1010 is visible as is a portion of the CMOS image sensor 1080; however, most of the emission path is obscured in this view. As is evident from the figures, the objectives are arranged in two rows and hexagonally packed.

The configurations described above exemplify a read head wherein each of the microfluorometers includes at least one radiation source, a beam splitter and a detector, wherein the beam splitter is positioned to direct excitation radiation from the excitation radiation source to the objective and to direct emission radiation from the objective to the detector, wherein the excitation radiation and emission radiation are directed in mutually orthogonal directions. In the embodiments, exemplified in FIG. 8 and FIG. 9, the detectors for several microfluorometers are arranged on a first side of the read head that is opposite the common plane to which the objectives are focused, a subset of the radiation sources is arranged on a second side of the read head (the second side being orthogonal to the first side and orthogonal to the common plane) and a second subset of the radiation sources is arranged on a third side of the read head (the third side being opposite the second side, orthogonal to the first side and orthogonal to the common plane). Alternatively, and as exemplified in FIG. 4, the radiation sources for several microfluorometers are arranged on a first side of the read head that is opposite the common plane to which the objectives are focused, a first subset of the detectors is arranged on a second side of the read head (the second side being orthogonal to the first side and orthogonal to the common plane) and second subset of the detectors is arranged on a third side of the carriage (the third side being opposite the second side, orthogonal to the first side and orthogonal to the common plane).

Figure 10:
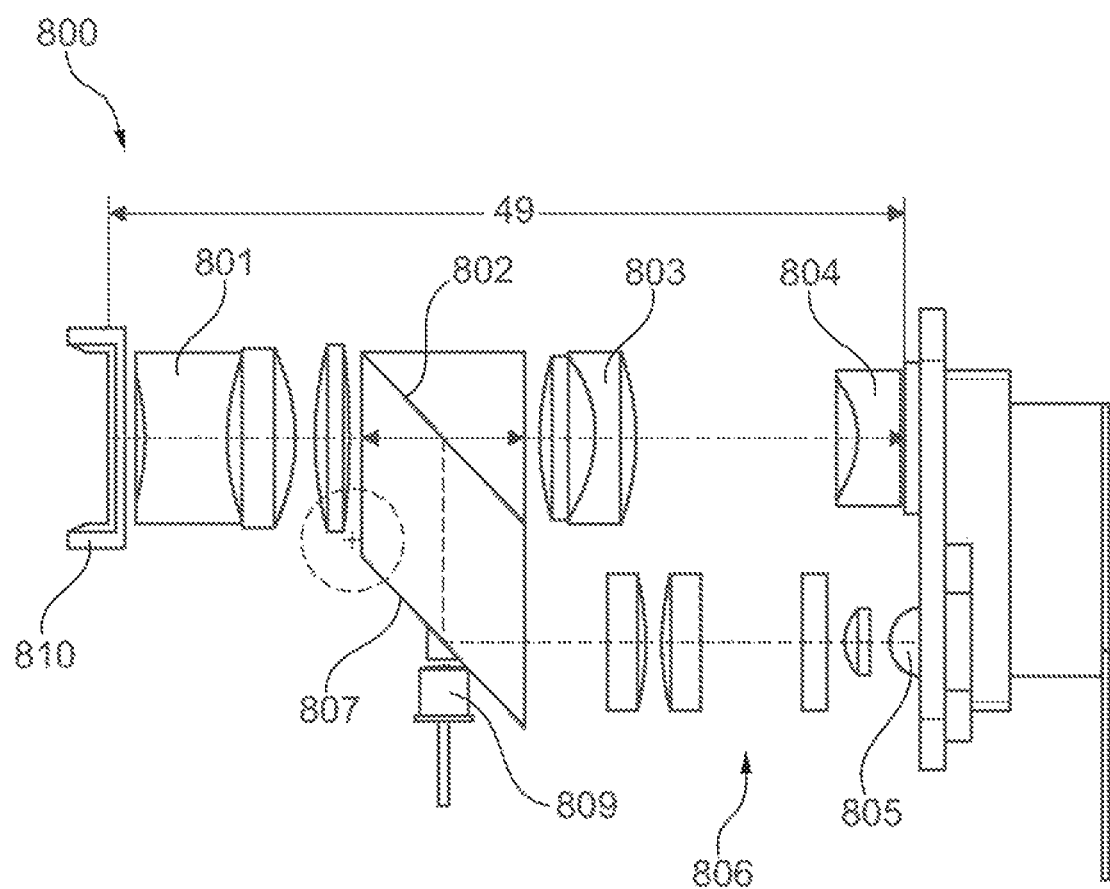
FIG. 10 shows an optical layout for an individual microfluorometer having parallel excitation and emission beam paths.

In addition to the embodiments above wherein the excitation and emission paths are orthogonal, configurations where emission and excitation paths are parallel can also be useful. In this case, the excitation radiation source(s) and detector can be present on the same side of the read head. An exemplary layout for a microfluorometer 800 is shown in FIG. 10, where excitation radiation from excitation source 805 passes through excitation optics 806 to prism surface 807 which reflects the excitation radiation to prism surface 802 which reflects the excitation radiation through objective 801. Emission passes through objective 801, then through beam splitter 802 to projection lens 803 and then to detector 804. The emission path is parallel to much of the excitation path. The detector and excitation radiation source are located on the same side of the microfluorometer, opposite and parallel to the detection plane. A guide 810 is configured to interface with a flow cell or substrate to align the objective. A similar guide can be used in other microfluorometers set forth herein. The layout for microfluorometer 800 is exemplary for purposes of demonstrating a parallel arrangement of excitation and emission paths. Other components can be included such as those shown in other figures herein including, but not limited to an autofocus module. For example, an excitation source 809 for an autofocus module is shown and produces excitation that passes through prism surface 807 and is reflected by prism surface 802 to pass through objective 801. Several microfluorometers 800 can be arranged to have objectives in one or more lines as exemplified in FIG. 6 and FIG. 7.

As demonstrated by the exemplary embodiments above, a read head can include a plurality of objectives, each objective being dedicated to a single microfluorometer. Thus, a microfluorometer of the present disclosure can include a variety of optical components, such as one or more detectors, excitation radiation sources, beam splitters lenses, mirrors, or the like, that form an optical train that directs excitation radiation through a single objective and/or that receives emission radiation through a single objective. In such embodiments, the objective can be configured as a macro-lens having a wide field of view. In alternative embodiments, a microfluorometer of the present disclosure can include a variety of optical components that directs excitation radiation through several objectives and/or that receives emission radiation through several objectives. Thus, an individual microfluorometer can include several optical trains that include several objectives. In embodiments that include several objectives per microfluorometer, the objectives can optionally be configured as an array of micro-lenses. Each objective among several in a particular microfluorometer (e.g. each micro-lens in an array of microlenses) can optionally be configured for independent focusing, whereby each objective can be moved in the z dimension independent of other objectives in the same microfluorometer. Alternatively or additionally, the several objectives can be configured for global focus such that they can all be moved together in the z dimension.

It will be understood that the various components of a read head that are set forth herein can be mixed and matched in various ways to achieve similar function to those exemplified herein. For example, as set forth in the previous paragraph, a read head can include several objectives and each of those objectives can be dedicated to a single microfluorometer or, alternatively, several of those objectives can be shared by a single microfluorometer. Similarly, and as set forth previously herein, each microfluorometer can include at least one dedicated excitation source or, alternatively, two or more microfluorometers can receive excitation radiation from a shared radiation source. Thus, there need not be a one to one correspondence between the number of microfluorometers in a particular read head and the number of components exemplified herein for any microfluorometer embodiment. Instead, one or more of the components exemplified herein as being useful in a microfluorometer can be shared by several microfluorometers in a particular read head.

A read head of the present disclosure is particularly useful for scanning methods and apparatus, for example, due to its relatively compact size and low mass which provides low inertia. Reduced inertia allows the read head to come to rest more quickly following movement, thereby allowing high resolution images to be obtained more rapidly than would be the case for a higher inertia read head for which residual movement of the read head would cause blurring and loss of resolution. Configurations for achieving movement of the read head will be set forth in further detail below. However, first it should be noted that the advantage of low inertia, is not intended to be a limitation or requirement for an apparatus or method set forth herein. Rather, a read head of the present disclosure can be maintained in a static position for all or part of a detection protocol. For example, a sequencing method, such as those using the fluidic and imaging steps set forth herein, can be carried out using a read head that is static during at least one and perhaps all of the cycles of the sequencing method.

As a first example of a static read head embodiment, a read head can include a sufficient number of microfluorometers to detect or image a desired portion of a surface or other object. Thus, the read head need not move in the x or y dimensions. For example, several microfluorometers can be linearly arranged to capture image frames along the full length (or at least along the effective target length) of a flow cell channel. Similarly, using an appropriate packing arrangement of several rows of microfluorometers, such as those set forth herein, several flow cell channels (present in one or more flow cell) can be imaged along their full length (or at least along the effective target length). As set forth previously herein, the image frames obtained for an individual channel can be, but need not be, contiguous.

As a second example of a static read head embodiment, a read head can remain at a fixed position with respect to the x and y dimensions while a substrate that is being detected by the read head is translated in the x and or y dimension. For example, an apparatus can be provided having a translation stage that is configured to present a substrate to the read head. The translation stage can move in a step-and-shoot or continuous motion to allow scanning of the substrate by the static read head. In particular embodiments, the substrate is a flow cell that can be affixed to the translation stage. The flow cell can be translated as part of a fluidic cartridge, such as those exemplified below, or the flow cell can be translated independently of any fluidic cartridge. Thus, the translation stage may be configured to affix a fluidic cartridge to which a flow cell is attached and to move the fluidic cartridge along with the flow cell or the translation stage can be configured to move only the flow cell while the fluidic cartridge remains in a static or fixed position.

In accordance with the above examples, relative motion between a scan head (or microfluorometer) and a substrate can be achieved by physical movement of the scan head (or microfluorometer), physical movement of the substrate, or physical movement of both. It will be understood that the static read heads referred to in the first and second exemplary embodiments above need not be static with respect to movement in the z dimension. Rather the static read heads can include one or more microfluorometers having autofocus modules. Alternatively or additionally, the read heads can be moved as a whole in the z dimension, for example, to achieve global focus at least to a rough approximation.

Figure 11:
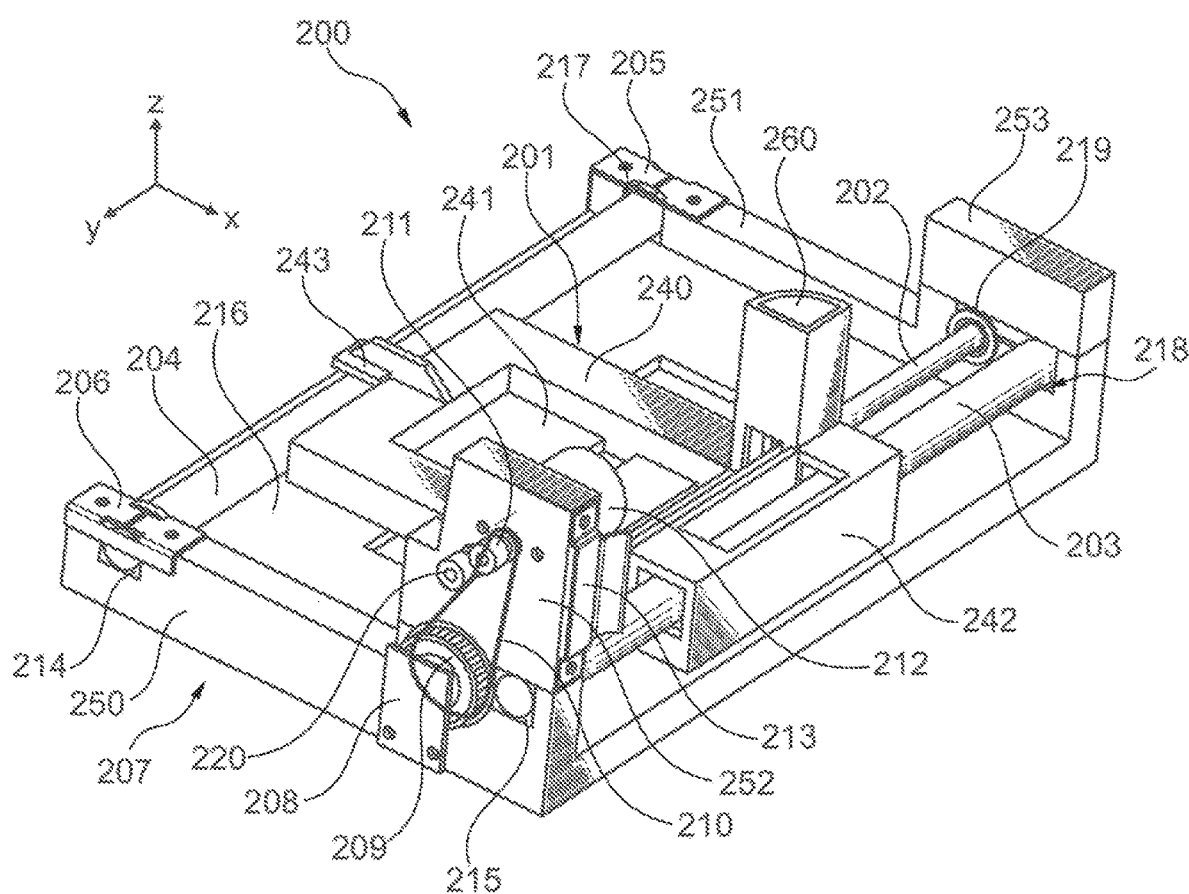
FIG. 11 shows a top perspective view of a Y-stage for a detection apparatus.
Figure 12:
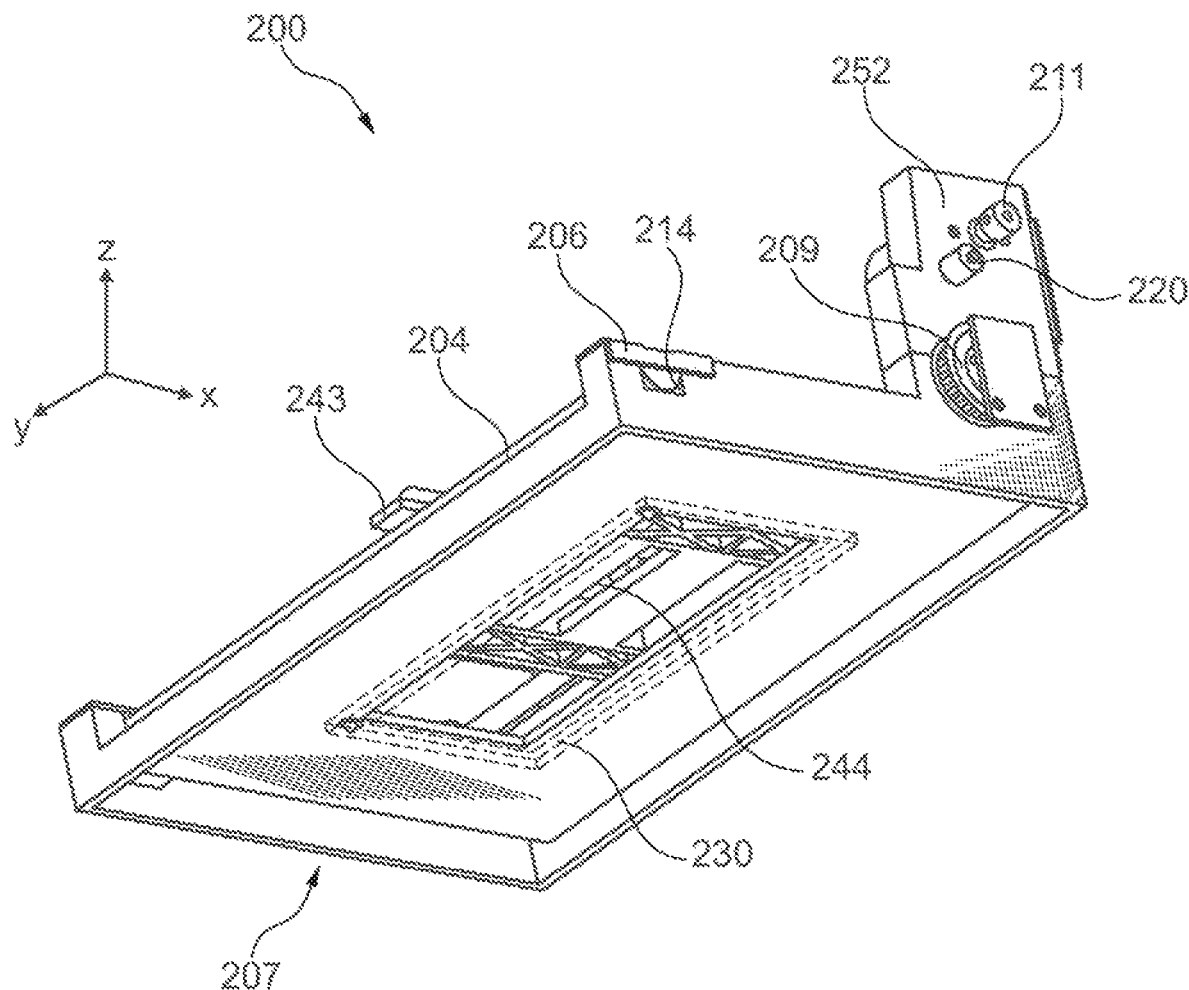
FIG. 12 shows a bottom perspective view of a Y stage for a detection apparatus.

Returning now to embodiments wherein a read head is translated, FIG. 11 and FIG. 12 show top and bottom views, respectively, of an exemplary y translation stage 200 for a read head. In this exemplary embodiment, the y stage is configured for translation in the y dimension but not in the x dimension. Thus, a read head carried by y translation stage 200 will be capable of movement in the y dimension and the read head or individual microfluorometers therein may be capable of movement in the z dimension (e.g. via autofocusing), but the read head will not be capable of movement in the x dimension. A read head can be affixed to carriage 201 having a base area 241 positioned to support the bottom side of the read head and a frame 240 configured to restrain the read head from side to side motion. The carriage 201 further includes a flange guide 243 and a collar guide 242. An opening 244 in base area 241 provides a window between a read head and substrate to be detected by the read head. The aforementioned components of the carriage 201 can form a monolithic structure.

The carriage is configured to move along a y stage frame 207 via a first shaft 203, along which the collar guide 242 runs and a second shaft 204 along which the flange guide 243 runs. The shafts are oriented along the y axis such that the carriage 201 is directed to slide back and forth along the y dimension via the guides. The first shaft 203 is held to the y stage frame 207 by insertion into datum 215 in a first side wall 250 and into datum 218 in a second sidewall 251. The first shaft 203 is clamped into datum 215 by support member 252 and clamped into datum 218 by support member 253. The second shaft 204 is held to the y stage frame 207 by insertion into datum 214 in a first side wall 250 and into datum 217 in a second sidewall 251. The first shaft 204 is clamped into datum 214 by shaft clamp 206 and clamped into datum 217 by shaft clamp 205.

Movement of carriage 201 is driven by rotation of lead screw 202 which is threaded through a lead nut 260 and which is affixed to the y stage frame 207 by insertion into a datum on the first side wall 250 and into a datum 219 in the second sidewall 251. The lead screw 202 is clamped in place by the same support members 252 and 253 that clamp the first shaft 203. The rotation of lead screw 202 is driven by motor 212 which is mounted to support member 252. An encoder 208 is configured to interact with the motor 212 via a belt 210 that interacts with rotor 209 on the encoder and rotor 211 on the motor 212. A belt tensioner 220 interacts with the belt 210.

An opening 230 passes through the floor 216 of y stage frame 207. The opening 230 is positioned to accommodate the trajectory of opening 244 in the base area 241 of the carriage 201 as it traverses the y stage frame. A read head is positioned in the carriage such that the objectives are directed through opening 244 and through opening 230 along a trajectory traversed by the carriage. Accordingly, the opening 230 accommodates imaging of an elongated area along the y axis via movement of a read head affixed to the carriage.

The structural and functional relationship between y translation stage 200 and read head 1000 is shown in FIG. 13. The orientation of the objectives 1010 with respect to the scanning direction of y translation stage 200 is similar to that exemplified in FIG. 7 (except that read head 1000 has an additional two objectives). A flow cell can be oriented with respect to y translation stage 200 as shown in FIG. 7.

As exemplified above a carriage can be configured to move a read head, for example, in a scanning operation. Alternatively or additionally, a carriage can be configured to prevent relative movement between individual microfluorometers of a read head in the x and y dimensions. A carriage need not provide this function, for example if the read head includes other structure elements that prevent relative transverse motion between individual microfluorometers. For example, a read head may be formed from a co-molded assembly. The co-molded assembly can in turn be affixed to a carriage. Nevertheless, in some embodiments, the carriage may play at least an auxiliary role in preventing relative transverse motion between individual microfluorometers of a read head. Furthermore it will be understood that a read head that is formed from a co-molded assembly can be used for embodiments that do not employ a carriage.

A y stage that is used in a method or apparatus set forth herein can be configured to scan via a discontinuous or continuous motion. Discontinuous scanning, often referred to as step-and-shoot scanning, generally involves incremental movement of a microfluorometer or scan head in the y (or x) direction and detection (e.g. image acquisition) between movements, while the microfluorometer or scan head is in a temporarily static state. Continuous scanning on the other hand generally involves detection or image acquisition while the microfluorometer or scan head is moving. In a particular embodiment continuous scanning can be carried out in time delay integration (TDI) mode. Accordingly, signal obtained by pixel elements along the scan dimension can be collected in a common bin and read out as a single value. TDI mode can provide advantages of increased signal processing rate and increased accuracy. Exemplary optical arrangements that can be included in a microfluorometer or read head to accommodate TDI mode detection are described, for example, in U.S. Pat. No. 7,329,860, which is incorporated herein by reference.

Movement of a microfluorometer or scan head in an x or y dimension, for example to accommodate continuous or discontinuous scanning modalities, can be controlled by an encoder or other device. In the example of y-stage 200, the motion can be controlled by encoder 208. As set forth previously herein, scanning (whether by continuous or discontinuous techniques) can result in acquisition of contiguous or non-contiguous frames from a substrate or other object under detection. Thus, the sum total of portions that are imaged by scanning can be contiguous (but not overlapping), non contiguous, or overlapping. The system need not be configured to obtain images of the entire substrate or object (e.g. array surface) and need not do so in a way that allows a composite image to be produced.

Figure 14:
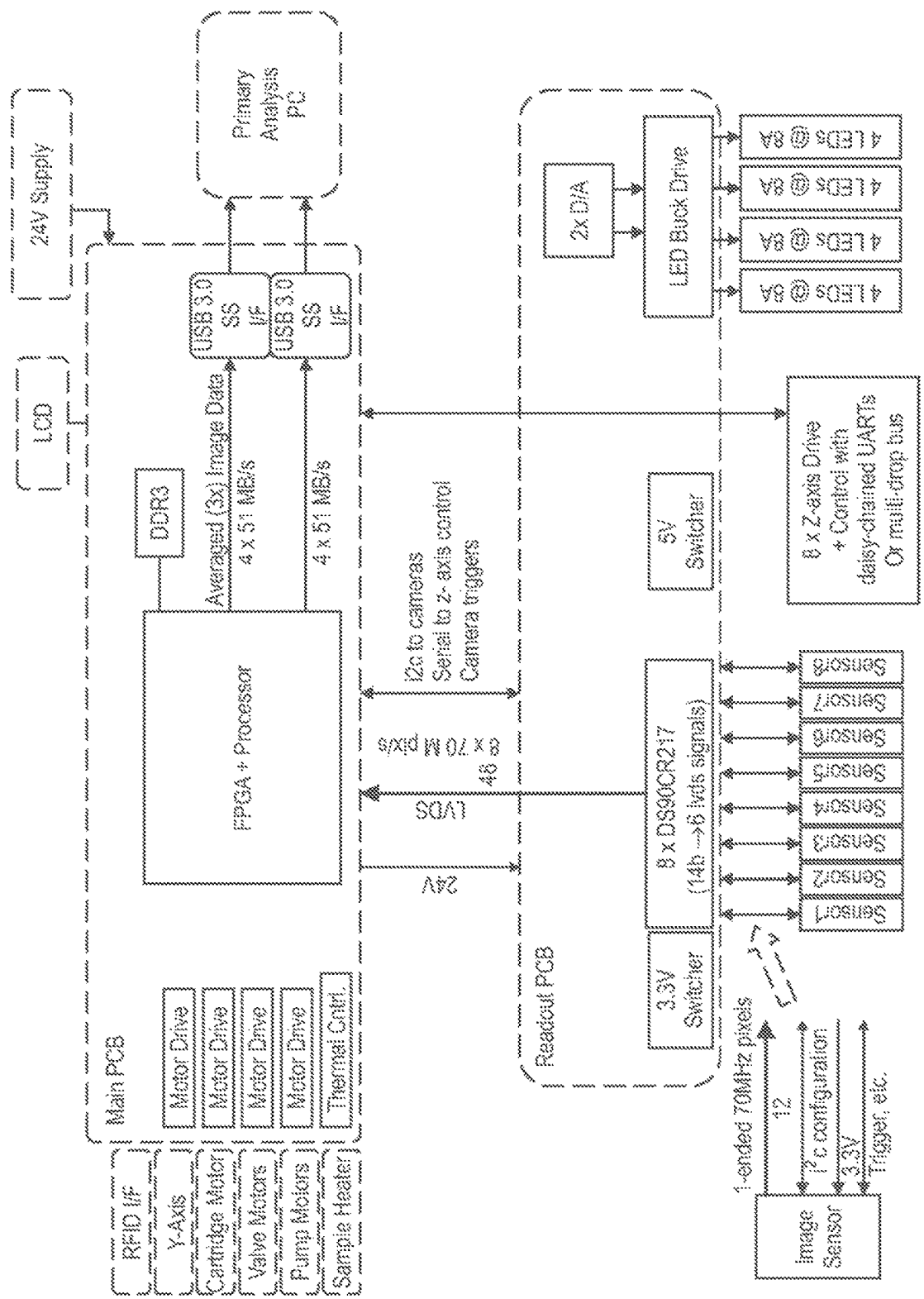
FIG. 14 shows an electrical block diagram for a detection apparatus.

An electrical block diagram for a detection apparatus is shown in FIG. 14. A readout printed circuit board (PCB) is present in a read head (see, for example, PCB 1701 and 1702 in FIG. 8) and is connected to a main PCB that is typically contained within the detection apparatus housing. In alternative embodiments the main PCB can be located exterior to the instrument. Data can be communicated between the readout PCB and main PCB via the LVDS line. For example, a 0.5 mm-pitch, 36-cond flat flex cable (FFC) can be used for the LVDS line. The LVDS line can be configured to communicate image data from the readout PCB to the main PCB, and instructions for camera control from the main PCB to the readout PCB. The two PCBs are also connected by a power line such as a copper-backed 1 mm-pitch 30-cond FFC that transmits power from a 24 volt power supply via the main PCB. The FFC connections are configured to have sufficient length and flexibility to allow the readout PCB to move with the read head while the main PCB remains stationary.

In the example of FIG. 14, the main PCB is also connected to an exterior primary analysis personal computer (PC) via USB 3.0 SS I/F connectors. In some embodiments the primary analysis computer can be located within the housing of the detection apparatus. However, placing the primary analysis computer off-instrument allows for interchangeable use of a variety of computers to be used for different applications, convenient maintenance of the primary analysis computer by replacement without having to interrupt the activity of the detection apparatus and small footprint for the detection apparatus. Any of a variety of computers, can be used including, for example, a desktop computer, laptop computer, or server containing a processor in operational communication with accessible memory and instructions for implementation of the computer implemented methods described herein. The main PCB is also connected to a liquid crystal display (LCD) for communication to a human user. Other user interfaces can be used as well.

In some embodiments, a user interface may include a display (e.g. an LCD) to display or request information from a user and a user input device (e.g. a keyboard) to receive user inputs. In some embodiments, the display and the user input device are the same device. For example, the user interface may include a touch-sensitive display configured to detect the presence of an individual's touch and also identify a location of the touch on the display. However, other user input devices may be used, such as a mouse, touchpad, keyboard, keypad, handheld scanner, voice-recognition system, motion-recognition system, and the like.

The readout PCB includes eight DS90CR217 transmitters for transferring data from individual sensors (i.e. detectors) to the LVDS line, 3.3 volt switching regulator, a 5 volt switching regulator, and LED buck drives for the LED excitation radiation sources.

The main PCB includes an FPGA+processor configured to accept image data from the LVDS. A DDR3 DIMM frame buffer is electronically connected to the FPGA+processor. The main PCB also includes a thermal control regulator and control circuitry for various drive motors such as a y-axis motor, cartridge motor, valve motor, and pump motor.

This disclosure further provides a method of imaging a substrate, including the steps of (a) providing a substrate including fluorescent features on a surface; (b) acquiring a plurality of wide-field images of a first portion of the surface using a plurality of microfluorometers, wherein each of the microfluorometers acquires a wide-field image from a different location of the surface, wherein the plurality of microfluorometers are affixed to a carriage; and (c) translating the carriage in a direction parallel to the surface and repeating (b) for a second portion of the surface. The method can use any of the apparatus set forth elsewhere herein, but need not be so limited in all embodiments.

Embodiments of the present methods find particular use for nucleic acid sequencing techniques. For example, sequencing-by-synthesis (SBS) protocols are particularly applicable. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates can be subjected to an SBS technique on a surface under conditions where events occurring for different templates can be distinguished. For example, the templates can be present on the surface of an array such that the different templates are spatially distinguishable from each other. Typically the templates occur at features each having multiple copies of the same template (sometimes called "clusters" or "colonies"). However, it is also possible to perform SBS on arrays where each feature has a single template molecule present, such that single template molecules are resolvable one from the other (sometimes called "single molecule arrays").

Flow cells provide a convenient substrate for housing an array of nucleic acids. Flow cells are convenient for sequencing techniques because the techniques typically involve repeated delivery of reagents in cycles. For example, to initiate a first SBS cycle, one or more labeled nucleotides, DNA polymerase, etc., can be flowed into/through a flow cell that houses an array of nucleic acid templates. Those features where primer extension causes a labeled nucleotide to be incorporated can be detected, for example, using methods or apparatus set forth herein. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary sequencing techniques are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

For the nucleotide delivery step of an SBS cycle, either a single type of nucleotide can be delivered at a time, or multiple different nucleotide types (e.g. A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, microfluorometer or read head need only provide excitation at a single wavelength or in a single range of wavelengths. Thus, a microfluorometer or read head need only have a single excitation source and multiband filtration of excitation need not be necessary. For a nucleotide delivery configuration where delivery results in multiple different nucleotides being present in the flow cell at one time, features that incorporate different nucleotide types can be distinguished based on different fluorescent labels that are attached to respective nucleotide types in the mixture. For example, four different nucleotides can be used, each having one of four different fluorophores. In one embodiment the four different fluorophores can be distinguished using excitation in four different regions of the spectrum. For example, a microfluorometer or read head can include four different excitation radiation sources. Alternatively a read head can include fewer than four different excitation radiation sources but can utilize optical filtration of the excitation radiation from a single source to produce different ranges of excitation radiation at the flow cell.

In some embodiments, four different nucleotides can be detected in a sample (e.g. array of nucleic acid features) using fewer than four different colors. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detectable under particular conditions while a fourth nucleotides type lacks a label that is detectable under those conditions. In an SBS embodiment of the second example, incorporation of the first three nucleotide types into a nucleic acid can be determined based on the presence of their respective signals, and incorporation of the fourth nucleotide type into the nucleic acid can be determined based on absence of any signal. As a third example, one nucleotide type can be detected in two different images or in two different channels (e.g. a mix of two species having the same base but different labels can be used, or a single species having two labels can be used or a single species having a label that is detected in both channels can be used), whereas other nucleotide types are detected in no more than one of the images or channels. In this third example, comparison of the two images or two channels serves to distinguish the different nucleotide types.

The three exemplary configurations in the above paragraph are not mutually exclusive and can be used in various combinations. An exemplary embodiment is an SBS method that uses reversibly blocked nucleotides (rbNTPs) having fluorescent labels. In this format, four different nucleotide types can be delivered to an array of nucleic acid features that are to be sequenced and due to the reversible blocking groups one and only one incorporation event will occur at each feature. The nucleotides delivered to the array in this example can include a first nucleotide type that is detected in a first channel (e.g. rbATP having a label that is detected in the first channel when excited by a first excitation wavelength), a second nucleotide type that is detected in a second channel (e.g. rbCTP having a label that is detected in the second channel when excited by a second excitation wavelength), a third nucleotide type that is detected in both the first and the second channel (e.g. rb having at least one label that is detected in both channels when excited by the first and/or second excitation wavelength) and a fourth nucleotide type that lacks a label that is detected in either channel (e.g. rbGTP having no extrinsic label).

Once the four nucleotide types have been contacted with the array in the above example, a detection procedure can be carried out, for example, to capture two images of the array. The images can be obtained in separate channels and can be obtained either simultaneously or sequentially. A first image obtained using the first excitation wavelength and emission in the first channel will show features that incorporated the first and/or third nucleotide type (e.g. A and/or T). A second image obtained using the second excitation wavelength and emission in the second channel will show features that incorporated the second and/or third nucleotide type (e.g. C and/or T). Unambiguous identification of the nucleotide type incorporated at each feature can be determined by comparing the two images to arrive at the following: features that show up only in the first channel incorporated the first nucleotide type (e.g. A), features that show up only in the second channel incorporated the second nucleotide type (e.g. C), features that show up in both channel incorporated the third nucleotide type (e.g. T) and features that don't show up in either channel incorporated the fourth nucleotide type (e.g. G). Note that the location of the features that incorporated G in this example can be determined from other cycles (where at least one of the other three nucleotide types is incorporated). Exemplary apparatus and methods for distinguishing four different nucleotides using detection of fewer than four colors are described for example in U.S. Pat. App. Ser. No. 61/538,294, which is incorporated herein by reference.

In a sequencing method, a microfluorometer can acquire at least two wide-field images of the same area of a surface during each cycle, wherein each of the at least two wide-field images is acquired using different excitation or emission wavelengths. For example, during each cycle a microfluorometer can acquire two, three or four wide-field images of the same area of a surface during each cycle, wherein each of the two wide-field images detect fluorescence at different regions of the spectrum. Alternatively or additionally, a microfluorometer may acquire wide-field images that detect fluorescence at no more than two, three or four different regions of the spectrum for a given area of a surface during a given sequencing cycle. For example, a microfluorometer may excite an area of a flow cell surface with radiation in no more than two, three or four different regions of the spectrum during a given cycle and/or a microfluorometer may acquire wide-field images from a given area of a surface in no more than two, three or four different regions of the spectrum during a given cycle. Different wide-field images can be obtained at different times (e.g. sequentially) or in some embodiments two or more wide-field images can be obtained simultaneously.

In the context of the present disclosure "different wide-field images of an area" refers to two or more wide-field images of the same area that are acquired under different excitation and/or emission conditions. Alternatively, two or more separate wide-field images of the same area can be acquired under the same or at least similar excitation and emission conditions. For example, multiple frames can be obtained for an area of a given object under a given fluorescence detection condition and the frames can be co-added. Co-adding can provide the advantage of increasing signal to noise as compared to obtaining a single frame under the same conditions. A further example is that co-adding can be performed in conjunction with pulsed excitation to reduce photo-damage to the sample as compared to continuous excitation of the sample over a prolonged period of time (that may or may not achieve similar signal intensity or signal to noise ratio).

In some embodiments, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; US 2002/0055100; U.S. Pat. No. 7,115,400; US 2004/0096853; US 2004/0002090; US 2007/0128624; or US 2008/0009420, each of which is incorporated herein by reference. Another useful method for amplifying nucleic acids on a surface is rolling circle amplification (RCA), for example, as described in Lizardi et al., *Nat. Genet.* 19:225-232 (1998) and US 2007/0099208 A1, each of which is incorporated herein by reference. Emulsion PCR on beads can also be used, for example as described in Dressman et al., *Proc. Natl. Acad. Sci. USA* 100:8817-8822 (2003), WO 05/010145, US 2005/0130173 or US 2005/0064460, each of which is incorporated herein by reference.

As set forth above, sequencing embodiments are an example of a repetitive process. The methods of the present disclosure are well suited to repetitive processes. Some embodiments are set forth below.

This disclosure provides a method of imaging a substrate, including the steps of (a) providing a substrate including fluorescent features on a surface; (b) acquiring a plurality of wide-field images of a first portion of the surface using a plurality of microfluorometers, wherein each of the microfluorometers acquires a wide-field image from a different location of the surface, wherein the plurality of microfluorometers are affixed to a carriage; (c) translating the carriage in a direction parallel to the surface and repeating (b) for a second portion of the surface; and (d) returning the carriage to a position to acquire a second plurality of wide-field images of the first portion of the surface. Optionally, the method can further include a step of modifying the fluorescent features on the surface after (c) and before (d), wherein the second plurality of wide-field images are different from the first plurality of wide-field images.

In particular embodiments, steps (a) through (c) of the above method correspond to the detection step(s) of a sequencing technique. In a related embodiment, step (d) whereby the carriage is returned corresponds to a second cycle of a sequencing technique. In this example, the modification of the fluorescent features on the surface can include one or more of the biochemical steps of a sequencing technique. Exemplary sequencing techniques that can be used in the method are set forth above or otherwise known in the art.

Also provided is a fluidics cartridge that includes (a) a flow cell having an optically transparent surface, an inlet and an outlet; and (b) a housing made of a material that is optically opaque and impermeable to aqueous liquids, wherein the housing holds: (i) a sample reservoir; (ii) a fluidic line between the sample reservoir and the inlet of the flow cell; (iii) a plurality of reagent reservoirs in fluid communication with the flow cell via the inlet of the flow cell, (iv) at least one valve configured to mediate fluid communication between the reservoirs and the inlet of the flow cell; and (v) at least one pressure source configured to move liquids from the sample reservoir or the reagent reservoirs to the flow cell via the inlet of the flow cell, wherein an optically transparent window interrupts the housing and an inlet port interrupts the housing, wherein the inlet port is in fluid communication with the sample reservoir, and wherein the optically transparent surface is positioned in the window.

Figure 15:
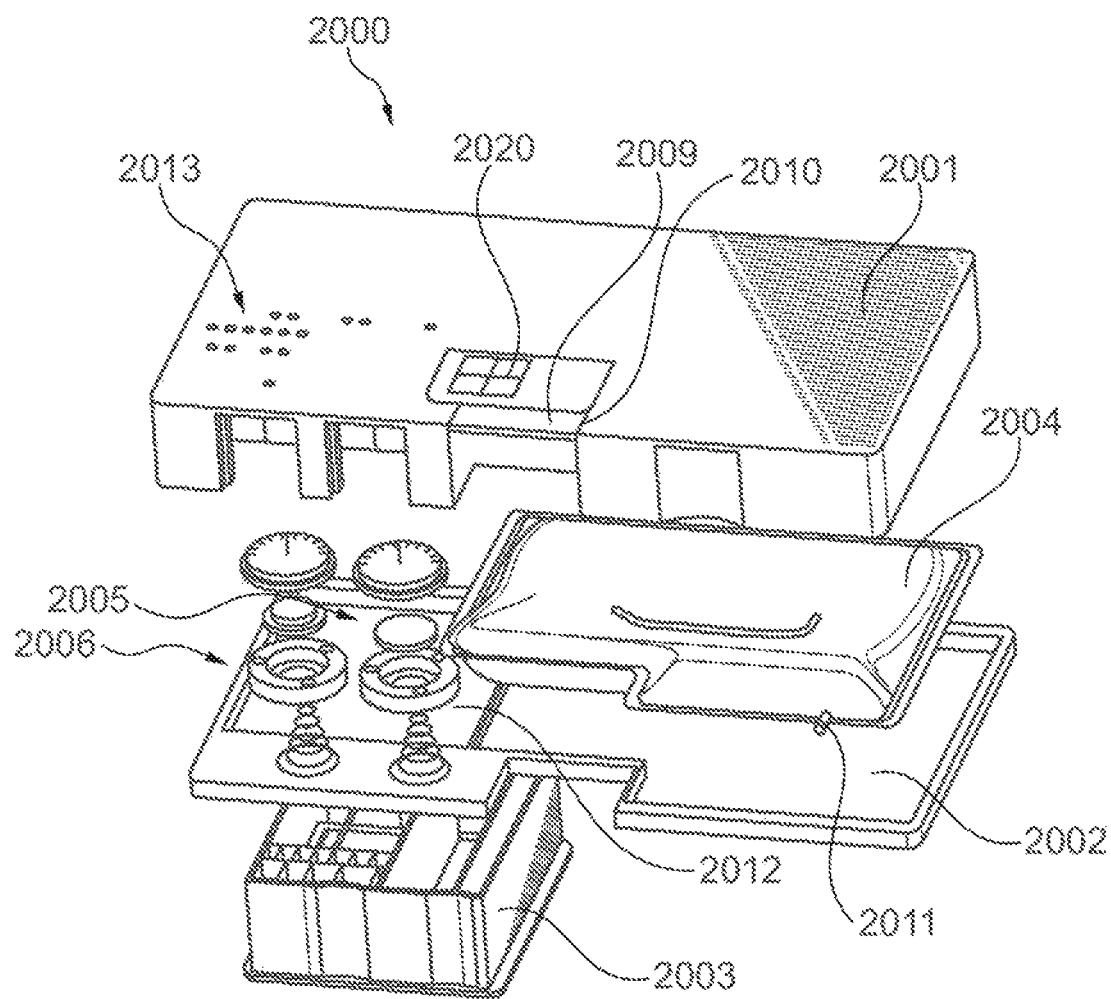
FIG. 15 shows an exploded view of a fluidic cartridge with flow cell.

The exterior view of an exemplary fluidics cartridge 10 is shown in FIG. 1 and is described above. FIG. 15 shows an exploded view of a fluidic cartridge 2000. The housing of the fluidic cartridge is formed by a shell 2001 that mates with a base 2002. The shell is on the upper side of the fluidic cartridge as shown and includes a reception area 2009 for a flow cell 2020. The flow cell is exposed to the exterior of the housing via a window 2010. One or more ports 2013 in the shell allow sample or other reagents to be delivered to the reservoirs in the interior of the fluidic cartridge 2000. The base 2002 includes an opening 2012 that is configured to accept a reagent tray 2003. The reagent tray 2003 can be engaged with the fluidic cartridge by insertion into the opening 2012 in a way that individual reagent reservoirs in the tray are in fluid communication with individual fluidic lines for delivery of reagents to the flow cell. The housing also contains valves 2005 and 2006 that interface with pumps to move the reagents through the fluidic lines. Also contained within the housing is a waste bag 2004 having an inlet 2011 that interfaces with fluidic lines from the flow cell 2020.

The housing of a fluidic cartridge (e.g. the shell 2001 and/or base 2002 of fluidic cartridge 2000) can be made of a material that is opaque to radiation in a particular part of the spectrum. For example, the housing may be opaque to UV, VIS and/or IR radiation in order to protect reagents from photo-damage due to radiation at these wavelengths. For example, a material that is opaque to UV radiation is beneficial for avoiding photo-damage to nucleic acids among other reagents used in sequencing reactions. As another example, it may be desirable to use a material that is opaque to radiation in the wavelength range absorbed by fluorophores used as labels in a sequencing reaction.

The housing for a fluidic cartridge will typically be impermeable to the liquids housed therein. Thus the housing can provide a secondary barrier in addition to the reservoirs held within. Exemplary materials include plastics such as polycarbonate or polystyrene, or metals such as aluminum or stainless steel. Materials that are chemically inert to the reagents housed in the fluidic cartridge are generally desirable. Individual reservoirs or other fluidic components in a fluidic cartridge will have similar properties of fluid impermeability and can optionally be opaque as well. The materials can be rigid or flexible. For example, any of a variety of the reagent reservoirs set forth herein or otherwise used in a fluidic cartridge can be a flexible bag as exemplified for waste reservoir 2004.

As exemplified by FIG. 1 and FIG. 15 a fluidic cartridge can be configured to contain a variety of components within a housing. For example, in various embodiments one or more of the fluidic components set forth herein can be fully contained within the housing. Indeed in particular embodiments all of the fluidic components of a particular embodiment can be fully contained in the fluidic cartridge. For example, a cartridge housing can contain one or more sample reservoirs, one or more reagent reservoirs, one or more waste reservoirs, one or more mixing reservoirs, one or more valves configured to mediate fluid communication between a reservoir and a flow cell, one or more pressure source configured to move liquids from a reservoir to a flow cell, or one or more fluidic lines between a reservoir and a flow cell. However, it will be understood that in some embodiments at least part of some fluidic components may be present outside of the housing. For example, a surface of a flow cell through which detection will occur can be outside of a cartridge housing.

In particular embodiments, a fluidic cartridge can include a reception area that is sized to tightly hold a flow cell, for example, by a compression fit. However, in other embodiments, the reception area can be larger than the footprint of a flow cell that is or will be present in the fluidic cartridge. Thus, the flow cell can occupy a reception space in the housing that is sized and shaped to permit the flow cell to float relative to the housing. A configuration that accommodates float of a flow cell can be advantageous for alignment of the flow cell with the optics component of a detection apparatus after the fluidic cartridge has been placed in the instrument. Alignment can be achieved by insertion of one or more alignment pins into the reception area by the detection apparatus for example in cases where the pins are pre-aligned to a microfluorometer of a read head of the detection apparatus. Accordingly, the reception area can include a fitting for at least one alignment pin or other alignment member. Exemplary configurations for aligning a floating flow cell that can be adapted to a fluidic cartridge of the present disclosure are described in U.S. Ser. No. 13/273,666 (published as US 2012/0270305 A1), which is incorporated herein by reference. In embodiments that utilize flow cell float, the fluidic connection from the flow cell to other fluidic components of the cartridge will generally be flexible. For example flexible tubing can connect a flow cell to fixed fluidic components of a cartridge.

A fluidic cartridge of the present disclosure need not include a detection device or other detection components described herein. For example, a fluidic cartridge can be configured to exclude a detector, microfluorometer or read head such as those described herein or those useful in a method set forth herein. In nucleic acid sequencing embodiments, a detector, microfluorometer or read head that is used to detect nucleic acids in a flow cell (or other substrate) of a fluidic cartridge can be located outside of the housing for the fluidic cartridge. Similarly for other embodiments, a detector, microfluorometer or read head that is used to detect a particular characteristic of a substrate can be excluded from the interior of a housing for a fluidic cartridge, being located external to the housing instead. It will be understood that in at least some configurations one type of detector can be excluded from a fluidic cartridge whereas another type of detector can be present. For example, a fluidic cartridge can exclude a detection device used to detect nucleic acids in a flow cell, but can include a detector used to evaluate a characteristic of a fluid in the cartridge or to evaluate a component of the cartridge. More specifically, a cartridge can include a detector for temperature, pressure, flow rate or other characteristics of the fluids used in the cartridge. Other examples of components that can be excluded from a fluidic cartridge include, but are not limited to, optical fitters, lenses, objectives, cameras (e.g. CCD cameras or CMOS cameras), excitation radiation sources (e.g. LEDs) or the like.

Figure 16:
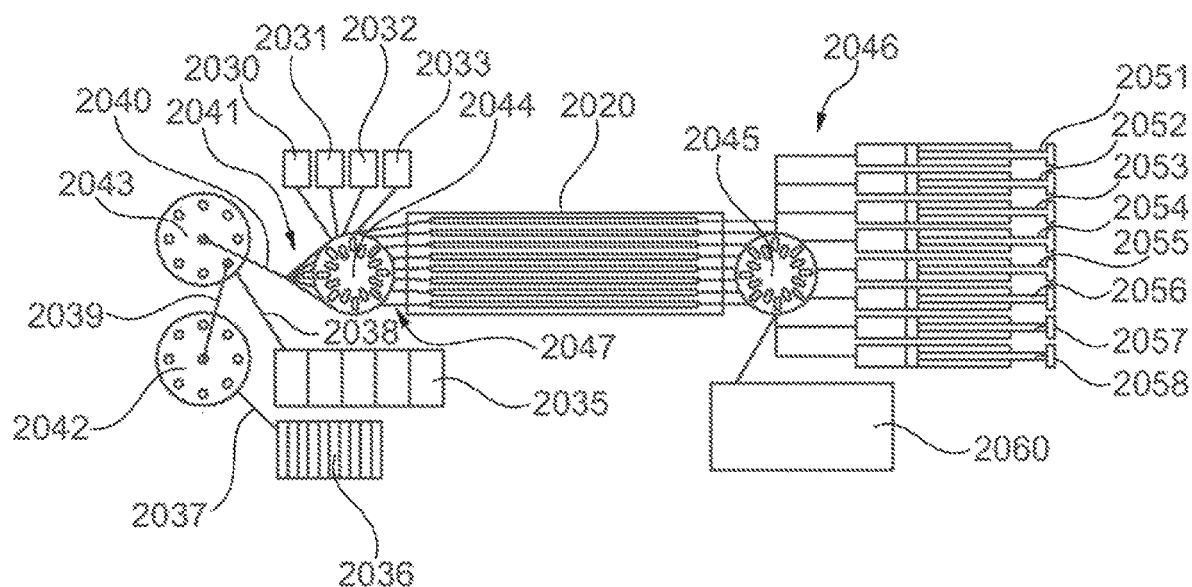
FIG. 16 shows a fluidics map for a fluidic cartridge.

A fluidic map for an exemplary fluidic cartridge is shown in FIG. 16. Flow cell 2020 has eight lanes each fluidically connected to one of eight individual fluid lines (collectively labeled 2047) that are individually actuated by inlet valve 2044. Inlet valve 2044 controls the flow of fluid from four sample reservoirs 2030 through 2033. Inlet valve 2044 also controls the flow of fluid from several SBS reagent reservoirs 2035 and from several amplification reagent reservoirs 2036. Distribution and flow of fluids from the SBS reagent reservoirs 2035 is controlled by reagent selection valve 2043. Distribution and flow of fluids from the amplification reagent reservoirs 2036 is controlled by reagent selection valve 2042 which is located upstream of reagent selection valve 2043. Accordingly reagent selection valve 2043 is positioned to control distribution and flow of reagents from both the SBS reagent reservoirs 2035 and the amplification reagent reservoirs 2036.

Flow of fluids through the system of FIG. 16 is driven by eight separate syringe pumps 2051 through 2058. The syringe pumps are positioned to pull fluids through the fluidic system and each pump can be individually actuated by valve 2045. Thus, flow though each channel of the flow cell can be individually controlled by a dedicated pressure source. Valve 2045 is also configured to control flow of fluids to waste reservoir 2060.

FIG. 16 exemplifies a fluidic system in which fluids are pulled by the action of downstream syringe pumps. It will be understood that a useful fluidic system can use other types of devices instead of syringe pumps to drive fluids including, for example, positive or negative pressure, peristaltic pump, diaphragm pump, piston pump, gear pump or Archimedes screw. Furthermore, these and other devices can be configured to pull fluids from a downstream position with respect to a flow cell or to push fluids from an upstream position.

FIG. 16 also exemplifies the use of eight syringe pumps for eight channels of a flow cell. Thus, the fluidic system includes a number of pumps that is equivalent to the number of channels in use. It will be understood that a fluidic system that is useful in a fluidic cartridge of the present disclosure can have fewer pumps (or other pressure sources) than the number of channels in use. For example, several channels can be fluidically connected to a shared pump and a valve can be used to actuate fluid flow through an individual channel.

Figure 17:
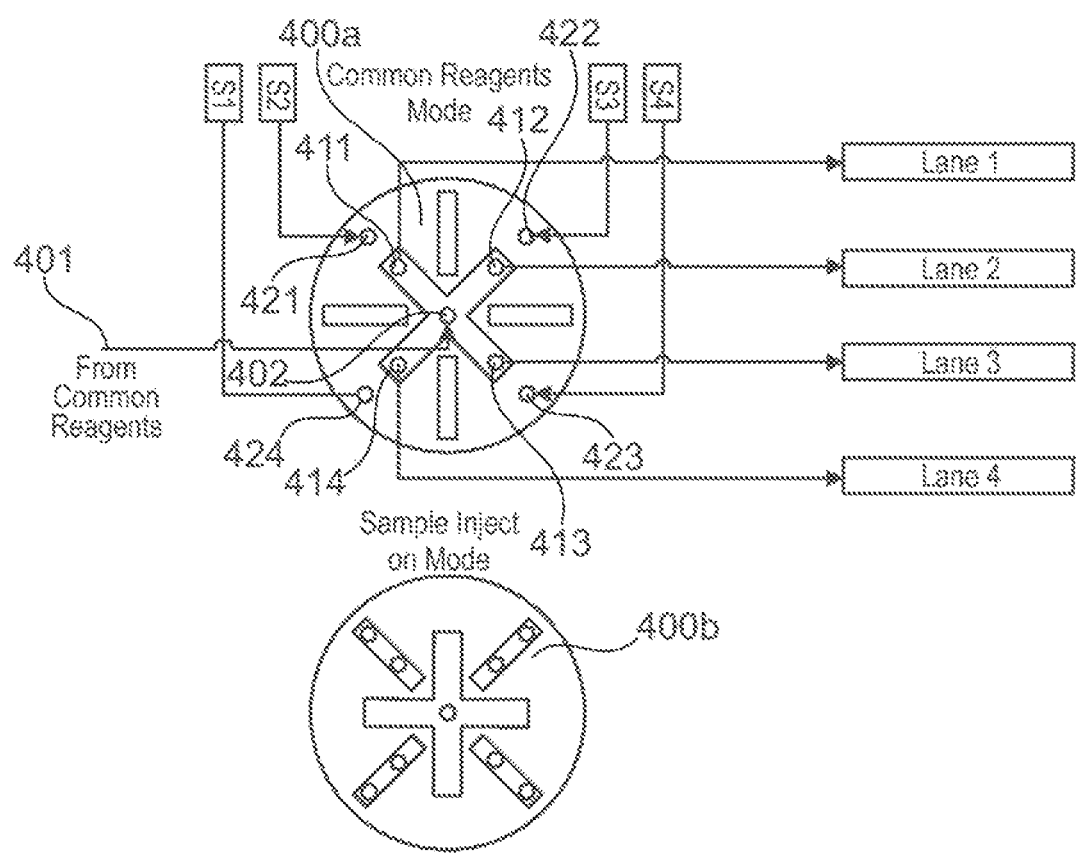
FIG. 17 shows a four-sample injection rotary valve.

An exemplary rotary valve 400 is shown in FIG. 17. The structure and function of rotary valve 400 can be understood in the context of a sequencing procedure as set forth below. Of course it will be understood that the valve can be used in similar ways for other applications. In a sequencing protocol where four different samples are to be fluidically processed, rotary valve 400 can function as a four-sample injection rotary valve using a 45 degree pitch and can also function as a four to one manifold for sequencing reagents. In the top view of FIG. 17, rotary valve 400a is positioned to allow flow from common reagent reservoir 401 to four lanes of a flow cell. More specifically, in this position, fluids can flow from common reagents 401 through port 402 to Lane 1 (via port 411), to Lane 2 (via port 412), to Lane 3 (via port 413), and to Lane 4 (via port 414). However, in this position fluids do not flow from sample reservoirs S1, S2, S3 or S4 because ports 421, 422, 423 and 424 are closed to flow from port 402. A 45 degree turn places rotary valve 400b to the position shown in the bottom view of FIG. 17, thereby allowing the samples S1, S2, S3 and S4 to be injected because ports 411, 412, 413 and 414 are open to flow from ports 421, 422, 423 and 424, respectively. However, in this position flow from port 402 is closed, thereby preventing flow of common reagents to the lanes of the flow cell.

Figure 18:
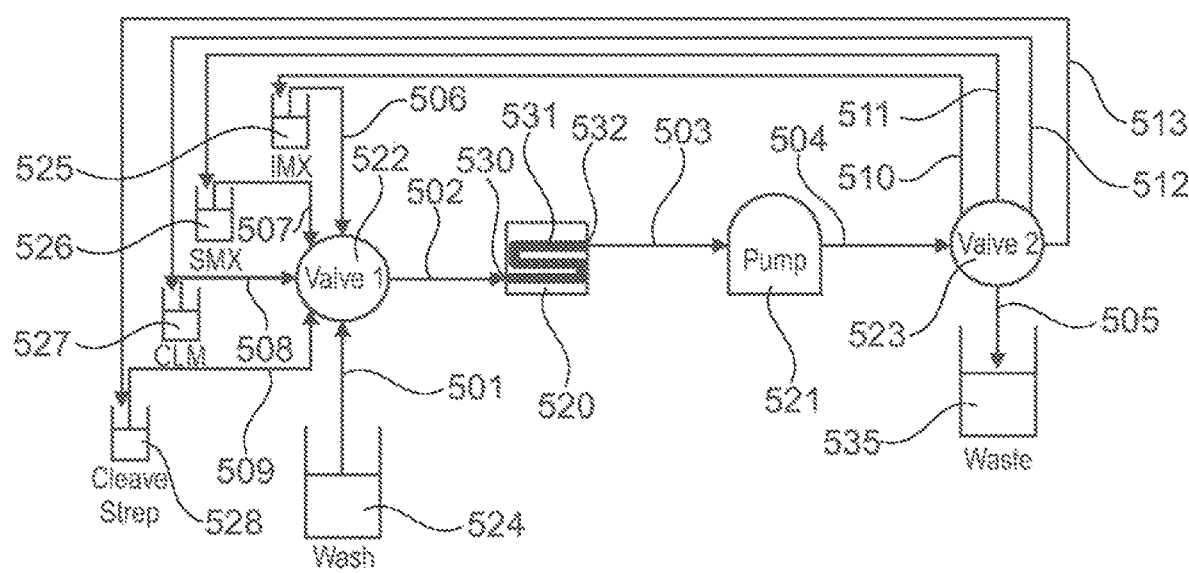
FIG. 18 shows a fluidics map for a reagent re-use system using unidirectional flow and two valves.

In particular embodiments a fluidic cartridge can be configured to allow re-use of one or more reagents. For example, the fluidic cartridge can be configured to deliver a reagent to a flow cell, then remove the reagent from the flow cell, and then re-introduce the reagent to the flow cell. In one configuration, as exemplified in FIG. 18, cartridge fluidics can be configured such that a reagent reservoir is in fluid communication with the input port of a flow cell and the output port of the flow cell is also in fluid communication with the reagent reservoir. One or more of the reagents can be re-used in a manifold network of similar reagent loops as shown in FIG. 18. For example, valve 522 controls flow from wash reservoir 524, IMX reservoir 525, SMX reservoir 526, CLM reservoir 527 and cleave reservoir 528 to flow cell 520. Pump 521 is downstream of flow cell 520 and upstream of valve 523. Valve 523 controls flow from flow cell 520 to waste reservoir 535, IMX reservoir 525, SMX reservoir 526, CLM reservoir 527 and cleave reservoir 528.

The fluidic lines connecting the above components of FIG. 18 will be described here in the context of a sequencing cycle where reagents are delivered from the reservoirs to the flow cell and used reagents are delivered from the flow cell to the respective reservoirs. In all steps of the cycle exemplified below fluids are moved under force of pressure produced by pump 521. In a first step of the cycle, the flow cell is washed by opening valve 522 to line 501 and opening valve 523 to line 505 such that fluid flows from wash reservoir 524 to waste reservoir 535 via a path between valve 522 and valve 523 that crosses through flow cell 520. For all steps described for FIG. 18, the path between valve 522 and valve 523 leads from valve 522 to line 502, to the inlet 530 of flow cell 520, through channel 531 of flow cell 520, through outlet 532 of flow cell 520, through line 503, to pump 521 and then through line 504 to valve 523. In a second step of the cycle, IMX is introduced to the flow cell by opening valve 522 to line 506 and opening valve 523 to line 505 such that fluid flows from IMX reservoir 525 to waste reservoir 535 via the path between valve 522 and valve 523 that crosses through flow cell 520. In a third step of the cycle, used IMX is moved from the flow cell 520 to IMX reservoir 525 by opening valve 522 to line 501 and opening valve 523 to line 510 such that wash fluid displaces IMX from the path between valve 522 and valve 523 that crosses through flow cell 520. In a fourth step of the cycle, SMX is introduced to the flow cell by opening valve 522 to line 507 and opening valve 523 to line 505 such that fluid flows from SMX reservoir 526 to waste reservoir 535 via the path between valve 522 and valve 523 that crosses through flow cell 520. In a fifth step of the cycle, used. SMX is moved from the flow cell 520 to SMX reservoir 526 by opening valve 522 to line 501 and opening valve 523 to line 511 such that wash fluid displaces SMX from the path between valve 522 and valve 523 that crosses through flow cell 520. Similar pairs of steps can be repeated to (1) introduce CLM reagent to the flow cell and to return used CLM reagent to the CLM reservoir, and (2) to introduce Cleave reagent to the flow cell and to return used. Cleave reagent to the Cleave reservoir.

Figure 19:
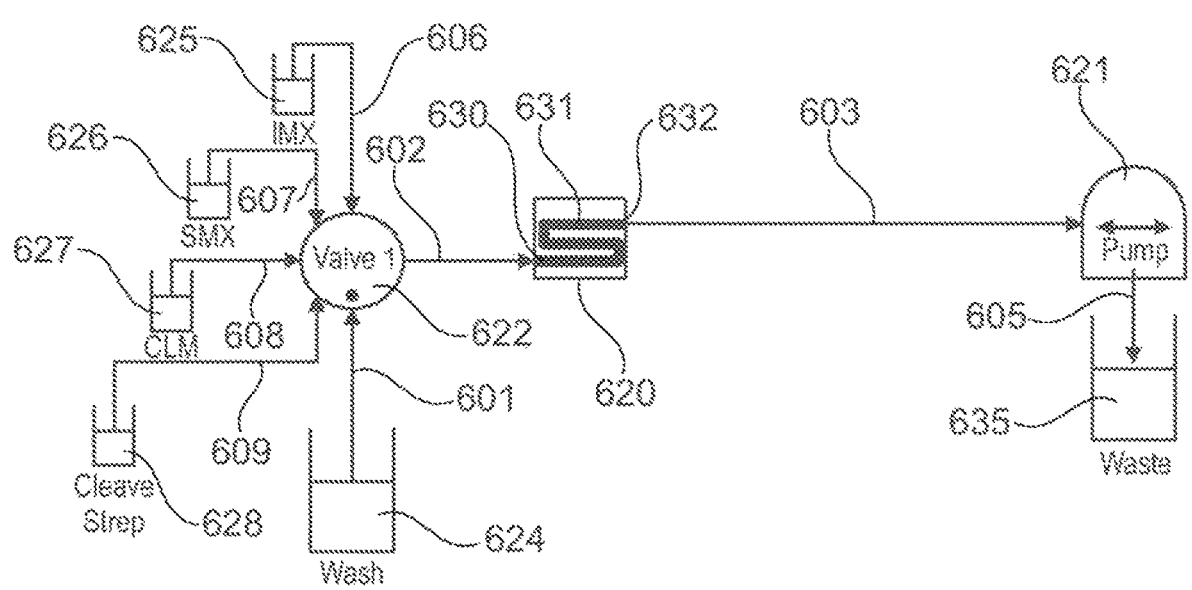
FIG. 19 shows a fluidics map for a reagent re-use system using reciprocating flow and a single valve.

Another example of a fluidic configuration that provides reagent re-use is shown in FIG. 19. In this example, fluidics for a cartridge are configured such that each reagent reservoir is in fluid communication with a single port of the flow cell 620. Reciprocating flow allows each reagent to flow from a reservoir to the flow cell 620 and from the flow cell 620 back to the reservoir, wherein ingress of reagents to the flow cell 620 and egress of the reagents from the flow cell 620 occur through the same port of the flow cell 620. Re-use for four reagents is exemplified in FIG. 19, however a fluidic system can be configured for more or fewer reagents to be re-used in a similar reciprocating format. As shown in FIG. 19, valve 622 controls flow of fluids between flow cell 620 and each of: wash reservoir 624, IMX reservoir 625, SMX reservoir 626, CLM reservoir 627 and cleave reservoir 628. In a first direction of flow, pump 621 is configured to pull fluids from flow cell 620 via line 603 and to push fluids to waste reservoir 635 via line 605.

The fluidic lines connecting the above components of FIG. 19 will be described here in the context of a sequencing cycle where reagents are delivered from the reservoirs to the flow cell and used reagents are delivered from the flow cell to the respective reservoirs. In a first step of the cycle the flow cell is washed by opening valve 622 to line 601 such that fluid flows from wash reservoir 624 to waste reservoir 635. The path between valve 622 and waste reservoir 635 leads from valve 622 to line 602 to port 630 of flow cell 620, through channel 631 of flow cell 620, through port 632 of flow cell 620, through line 603 to pump 621 and then through line 605 to waste reservoir 635. In a second step of the cycle, IMX is introduced to the flow cell by opening valve 622 to line 606 such that fluid flows from IMX reservoir 625 through valve 622 to line 602, to port 630 of flow cell 620, through channel 631 of flow cell 620, through port 632 of flow cell 620, and partially through line 603 (thereby leaving residual wash solution in a downstream portion of line 603 through to pump 621). In a third step of the cycle, used IMX reagent is returned from the flow cell 620 to IMX reservoir 625 by opening valve 622 to line 606 and reversing the direction of pump 621 such that used IMX reagent is returned from the flow cell 620 to the IMX reservoir 625 via port 630 of flow cell 620, to fluid line 602, through valve 622 then through fluid line 606 to IMX reservoir 625. During step three, flow from pump 621 to the IMX reservoir 625 occurs for sufficient time that a portion of the IMX reagent returns to the IMX reservoir 625, but not long enough to cause a substantial amount of the residual wash solution from line 603 to enter the IMX reservoir 625. In a fourth step of the cycle, the flow cell is washed as described for the first step. In a fifth step of the cycle, SMX is introduced to the flow cell by opening valve 622 to line 607 such that fluid flows from SMX reservoir 626 through valve 622 to line 602, to port 630 of flow cell 620, through channel 631 of flow cell 620, through port 632 of flow cell 620, and partially through line 603 (thereby leaving residual wash solution in a downstream portion of line 603 through to pump 621). In a sixth step of the cycle, used SMX reagent is returned from the flow cell 620 to SMX reservoir 626 by opening valve 622 to line 607 and reversing the direction of pump 621 such that used. SMX reagent is returned from the flow cell 620 to the SMX reservoir 626 via port 630 of flow cell 620, to fluid line 602, through valve 622 then through fluid line 607 to SMX reservoir 626. As with step three, flow from pump 621 during step six causes a portion of the SMX reagent to return to the SMX reservoir 626, but little to no residual wash solution from line 603 to enter the SMX reservoir 626. Similar triplets of steps can be repeated to (1) introduce CLM reagent to the flow cell 620, return used CLM reagent to the CLM reservoir 627 and wash the flow cell 620, and (2) to introduce Cleave reagent to the flow cell 620, return used. Cleave reagent to the Cleave reservoir 628 and wash the flow cell 620.

The examples of FIG. 18 and FIG. 19 show a single reservoir for each reagent. Accordingly, mixing of used reagents with unused reagents of the same type can occur throughout the fluidic process. In this embodiment, the fraction of re-used reagent in the reservoir will increase with each fluidic cycle. Accordingly, a sufficiently large volume of initial reagent can be provided to accommodate any dilution or contamination that may occur while maintaining a desired level of overall reaction quality.

As an alternative to the use of a single reservoir for each reagent, the fluidic system can include several reservoirs for each type of reagent. Each of the reservoirs can be configured for re-use. However, each reservoir can be subjected to a number of mixing events that is fewer than the number of cycles for the flow cell. Accordingly, an appropriate number of reservoirs for each reagent type can be provided to accommodate both a desired number of cycles for a flow cell and the limited number of cycles of re-use acceptable for each reagent. For example, ten reservoirs can be provided for a particular reagent in order to accommodate a fluidic process having one hundred cycles and a reagent that is to be used only ten times (i.e. re-used 9 times). In this example, once one of the ten reservoirs has been drawn from ten times the system can switch to a second of the ten reservoirs. Multiple reagent reservoirs can be configured for re-use in the exemplary system shown in FIG. 18, for example, by interfacing the additional reservoirs to valve 522 and valve 523 or by interfacing each subset of reservoirs with a dedicated valve upstream of valve 522 and downstream of valve 523. Taking the example of FIG. 19, multiple reagents can be configured for re-use by interfacing the additional reservoirs to valve 622 or by interfacing each subset of reservoirs with a dedicated valve upstream of valve 622 (in the flow cell input direction which is downstream of valve 622 in the flow cell output direction).

Another useful configuration for re-use of a given reagent is to utilize a supplemental reservoir that is separate from a reagent reservoir. Taking as an example the configuration of FIG. 18, lines 510, 511, 512 and 513 can flow to respective supplemental reservoirs such that reagents are not directed back to reagent reservoirs 525, 526, 527 and 528 after being contacted with the flow cell. The used reagent can then be delivered from the respective supplemental reservoirs to the flow cell via different ports in valve 522 or via a separate valve. Turning to the example of the fluidic system of FIG. 19, supplemental reservoirs can be added to the system and ports can be added to valve 622 to direct used reagents to the supplemental reservoirs. Accordingly, actuation of valve 622 can be used to direct used reagents to the supplemental reservoirs instead of to reagent reservoirs 625, 626, 627 and 628 after the reagents have been contacted with the flow cell. For embodiments that include a supplemental reservoir including but not limited to those exemplified in FIG. 18 and FIG. 19, used reagents (of a particular type) from several cycles can be mixed in the supplemental reservoirs prior to re-use. Alternatively, used reagents can be re-used sequentially absent mixing in the supplemental reservoirs. Whether or not used reagents are mixed, once reagents have been re-used a predetermined or otherwise desirable number of times, the used reagents can be sent to a waste reservoir and the supplemental reservoir used again for subsequent cycles with subsequent aliquot(s) of used reagent.

The configurations shown in FIG. 18 and FIG. 19 are exemplary. Other configurations are possible as well to achieve re-use of one or more of the reagents used in a particular process. It will be understood that in some reagent re-use configurations, fluidic configurations for reagent re-use will only be used for a subset of the reagents used in a particular process. For example, a first subset of the reagents may be robust enough to be re-used whereas a second subset may be prone to contamination, degradation or other unwanted effects after a single use. Accordingly, the fluidic system can be configured for re-use of the first subset of reagents, whereas the fluidics for the second set of reagents will be configured for single use.

A particular reagent can be re-used any number of times desired to suit a particular process. For example, one or more of the reagents exemplified herein, described in a reference cited herein, or otherwise known for use in a process set forth herein can be re-used at least 2, 3, 4, 5, 10, 25, 50 or more times. Indeed any of a variety of desired regents can be re-used for at least as many times.

Fluidic configurations and methods for reagent re-use, although exemplified for a nucleic acid sequencing process, can be applied to other processes, in particular processes that involve repeated cycles of reagent delivery. Exemplary processes include sequencing of polymers such as polypeptides, polysaccharides or synthetic polymers and also include synthesis of such polymers.

FIG. 18 and FIG. 19 and other examples provided herein with regard to methods and apparatus for reagent re-use have been described in the context of a single channel for a flow cell. It will be understood that similar methods and apparatus can be applied to a flow cell having multiple channels. Accordingly a fluidic cartridge of the present disclosure can include a flow cell having multiple channels and can further include a fluidic system configured to provide reagent re-use for all or a subset of the channels. For example, individual channels can be connected to a fluidic system configured as shown in FIG. 18 or FIG. 19 or as described elsewhere herein.

A fluidic cartridge of the present disclosure can include an input output (I/O) connection to enable communication between the fluidic cartridge and a detection apparatus that receives the fluidic cartridge. The I/O connection can be used to coordinate fluidic operations occurring in the fluidic cartridge with detection operations occurring in the detection apparatus. For example, in a nucleic acid sequencing procedure fluidic delivery of sequencing reagents to a flow cell can be coordinated with detection of the flow cell by the detection apparatus in one or more cycles of the sequencing procedure. In the embodiment of FIG. 14, the I/O connector can enable communication between the fluidic cartridge and the main PCB.

As will be evident from the exemplary nucleic acid sequencing embodiments set forth herein, reservoirs in a fluidic cartridge of the present disclosure can contain reagents useful for a nucleic acid sequencing procedure. For example, reagents useful for a sequencing-by-synthesis technique can be present including, for example, a polymerase, a fluorescently labeled nucleotide, or a wash solution. Several different fluorescently labeled nucleotides can be present either as a mixture in a single reservoir or each alone in a separate reservoir. The labeled nucleotides can have reversible terminating moieties for use in reversible terminator sequencing in which case a reservoir containing a deblocking agent can also be present. Other nucleic acid sequencing reagents that can be included in a fluidic cartridge include those set forth previously herein including, but not limited to those described in Bentley et aL., Nature 456:53-59 (2008); WO 04/018497; U.S. Pat. No. 7,057,026; WO 91/06678; WO 071123744; U.S. Pat. Nos. 7,329,492; 7,211,414; 7,315,019; 7,405,281, or US 2008/0108082, each of which is incorporated herein by reference. In particular, nucleic acid sequencing reagents available from ILLUMINA® such as those provided in TRUSEQ® SBS kits can be included in a fluidic cartridge.

The reservoirs of a fluidic cartridge can also include a nucleic acid sample that is to be sequenced. Several samples can be present each in their own reservoir. In some embodiments several samples can be mixed in a single reservoir, for example, in cases where the samples were previously tagged with known nucleic acid tag sequences and then mixed together.

A fluidic cartridge can also include reservoirs that contain reagents used for amplification of nucleic acids. For example, reagents used for bridge amplification (also called cluster amplification) can be included such as those described in U.S. Pat. No. 5,641,658; US 2002/0055100; U.S. Pat. No. 7,115,400; US 2004/0096853; US 2004/0002090; US 2007/0128624; or US 2008/0009420, each of which is incorporated herein by reference. In particular, bridge amplification reagents available from ILLUMINA® such as those provided in TRUSEQ®-RNA or DNA amplification kits can be included in a fluidic cartridge. Reagents useful for rolling circle amplification (RCA) can also be present in a fluidic cartridge including, for example, those described in Lizardi et al., Nat. Genet. 19:225-232 (1998) or US 2007/0099208 AI, each of which is incorporated herein by reference. Emulsion PCR reagents can also be used, for example, those described in Dressman et al., Proc. Natl. Acad. Sci. USA 100:8817-8822 (2003), WO 05/010145, or US 2005/0130173 or US 2005/0064460, each of which is incorporated herein by reference.

A fluidic cartridge of the present disclosure can include two or more sub-component parts that contain different reagents. The sub-component parts can be configured for convenient combination into a fluidic cartridge, for example, by hand and without the use of tools. For example, sub-component parts can be combined into a fluidic cartridge using pressure fitting, snapping together of complementary male and female fittings, insertion into appropriately sized receiving ports, clamping or the like. If desired, connections requiring tools can be used for example use of a screwdriver to connect with screws, or use of a wrench to turn a bolt and/or nut.

The sub-component parts that make up a fluidic cartridge can contain reagents that were previously transported and/or stored under different conditions. For example a first sub-component can include reagents that are stored at freezing temperatures (e.g. below 0° C., −20° C. or −70° C.) whereas a second sub-component can include reagents that are stored at a higher temperature (e.g. room temperature or above 20° C., 0° C., −20° C. or −70° C.). Accordingly, at least some of the reagents in reservoirs of one sub-component may be frozen solid, while all of the reagents in the reservoirs of another sub-component are in liquid form. Two or more subcomponent parts that have been stored at different temperatures can be combined into a fluidic cartridge before or after the temperatures equilibrate to ambient temperature (or other common temperature).

Reagents useful for fluidic processes other than nucleic acid sequencing processes can be provided in the reservoirs of a fluidic cartridge. For example a fluidic cartridge can contain reagents useful for sequencing of other polymers such as polypeptides, polysaccharides or synthetic polymers. Alternatively or additionally, reagents useful for the synthesis of such polymers can also be present.

However, returning to embodiments relating to nucleic acid sequencing this disclosure further provides a sequencing method that includes the steps of (a) providing a fluidic cartridge having (i) a flow cell having an optically transparent surface, (ii) a nucleic acid sample, (iii) a plurality of reagents for a sequencing reaction, and (iv) a fluidic system for delivering the reagents to the flow cell; (b) providing a detection apparatus having (i) a plurality of microfluorometers, wherein each of the microfluorometers comprises an objective configured for wide-field image detection in an image plane in x and y dimensions, and (ii) a sample stage; (c) delivering the fluidic cartridge to the sample stage, wherein the optically transparent surface is placed in the image plane; and (d) carrying out fluidic operations of a nucleic acid sequencing procedure in the fluidic cartridge and detection operations of the nucleic acid sequencing procedure in the detection apparatus, wherein (i) the reagents are delivered to the flow cell by the fluidic system, and (ii) the nucleic acid features are detected by the plurality of microfluorometers.

Any of a variety of detection apparatus and/or fluidic cartridges described herein can be used in the above method. A particular advantage of the apparatus set forth herein is modularity that allows for convenient sequencing of different samples using a single detection apparatus. As set forth previously herein, sample(s), reagents and fluidic hardware sufficient for an entire sequencing procedure can be self contained in a fluidic cartridge that can be delivered to a detection apparatus for a sequencing procedure. Once the sequencing procedure is completed the fluidic cartridge can be removed such that the detection apparatus is ready for another sequencing run. By separating the detection apparatus and fluidics system into separate modules, the present system allows multiple different samples to be sequenced while avoiding the risk of cross contamination between samples that occurs for existing systems where the detection apparatus and fluidic system are permanently integrated. Furthermore, for embodiments where the detection components are relatively expensive and technically difficult to assemble, the modularity set forth herein provides for cost savings by allowing the detection apparatus to be maintained for repeated use while the typically lower priced and easier to assemble fluidic components are replaced or discarded by an act that can be as simple as pressing an eject button.

Accordingly, a sequencing method can include the steps of (a) providing a fluidic cartridge having (i) a flow cell having an optically transparent surface, (ii) a nucleic acid sample, (iii) a plurality of reagents for a sequencing reaction, and (iv) a fluidic system for delivering the reagents to the flow cell; (b) providing a detection apparatus having (i) a plurality of microfluorometers, wherein each of the microfluorometers comprises an objective configured for widefield image detection in an image plane in x and y dimensions, and (ii) a sample stage; (c) delivering the fluidic cartridge to the sample stage, wherein the optically transparent surface is placed in the image plane; (d) carrying out fluidic operations of a nucleic acid sequencing procedure in the fluidic cartridge and detection operations of the nucleic acid sequencing procedure in the detection apparatus, wherein (i) the reagents are delivered to the flow cell by the fluidic system, and (ii) the nucleic acid features are detected by the plurality of microfluorometers; (e) removing the fluidic cartridge from the sample stage; (f) delivering a second fluidic cartridge to the sample stage; and (g) carrying out fluidic operations of a nucleic acid sequencing procedure in the second fluidic cartridge and detection operations of the nucleic acid sequencing procedure in the detection apparatus.

A second fluidic cartridge will generally include a second nucleic acid sample that is different from the nucleic acid sample in the first fluidic cartridge. However, if desired, two fluidic cartridges can include duplicate samples, for example, to provide for statistical analysis or other technical comparisons. A sequencing system or method of the present disclosure can be repeatedly used for a number of fluidic cartridges. For example, it is contemplated that at least 2, 5, 10, 50, 100, or 1000 or more fluidic cat fridges can be used.

In particular embodiments, a flow cell that contains a plurality of channels can be fluidically manipulated and optically detected in a staggered fashion. More specifically, the fluidic manipulations can be carried out on a first subset of the channels in the flow cell while optical detection occurs for a second subset of the channels. For example, in one configuration at least four linear channels can be disposed parallel to each other in the flow cell (e.g. channels 1 through 4 can be ordered in sequential rows). Fluidic manipulations can be carried out on every other channel (e.g. channels 1 and 3) while detection occurs for the other channels (e.g. channels 2 and 4). This particular configuration can be accommodated by using a read head that affixes several microfluorometers in a spaced apart configuration such that the objectives are directed to every other channel of the flow cell. In this case the read head can have a number of microfluorometers that is half the number of channels in the flow cell. Furthermore, valves can be actuated to direct flow of reagents for a sequencing cycle to alternating channels while the channels that are being detected are maintained in a detection state. In this example, a first set of alternating channels can undergo fluidic steps of a first sequencing cycle and a second set of alternating channels undergo detection steps of a second sequencing cycle. Once the fluidic steps of the first cycle are completed and detection steps of the second cycle are completed, the read head can be stepped over (e.g. along the x dimension) to the first set of alternating channels and valves can be actuated to deliver sequencing reagents to the second set of channels. Then detection steps for the first cycle can be completed (in the first set of channels) and fluidic steps for a third cycle can occur (in the second set of channels). The steps can be repeated in this way several times until a desired number of cycles have been performed or until the sequencing procedure is complete.

An advantage of the staggered fluidic and detection steps set forth above is to provide for a more rapid overall sequencing run. In the above example, a more rapid sequencing run will result from the staggered configuration (compared to fluidically manipulating all channels in parallel followed by detection of all channels in parallel) if the time required for fluidic manipulation is about the same as the time required for detection. Of course, in embodiments where the timing for detection steps is not the same as the timing for fluidic steps, the staggered configuration can be changed from every other channel to a more appropriate pattern to accommodate parallel scanning of a subset of channels while another subset of channels undergoes the fluidic steps.

In accordance with several embodiments set forth above, a detection apparatus having a relatively compact form factor is provided. In some embodiments, a detection apparatus can have a footprint that is about 1 square foot and can occupy a volume of about 1 cubic foot. Smaller areas and/or volumes are possible. Slightly larger footprint areas and/or volumes are also useful. As exemplified herein an apparatus can have a relatively small foot print and occupy a relatively small volume of space when it is in a fully functional state, for example, after accepting a fluidic cartridge internally. Several apparatus have been exemplified herein in the context of their use as stand-alone units capable of performing any of a variety of desired procedures. However, those examples are not intended to be limiting and indeed the compact form factor of embodiments set forth above allows several apparatus to be arranged in a small space. For example, several apparatus can be stacked and/or placed in a cabinet or rack for convenient placement. The cabinet or rack can include one or more shelves that each defines one or more reception spaces, and each reception space can be configured to accommodate one or more detection apparatus.

Accordingly, several detection apparatus of the present disclosure can be used together in a larger system, whereby each detection apparatus effectively functions as a module or node of the system. For example, several detection apparatus can be physically co-located in a rack and can be electronically networked. Electronic networking, whether for apparatus that are co-located or for apparatus that are located at distributed locations, can allow global data analysis and/or global control of instrument function. For nucleic acid sequencing embodiments, several different detection apparatus can function as a sequencing system, for example, to sequence the same sample (or sub-fractions of the same sample) in parallel. A nucleic acid sequencing system can include a control computer that provides instructions to each individual detection apparatus. As such, any one of the detection apparatus in the nucleic acid sequencing system can take instructions from a control computer that is physically external to that detection apparatus. Nucleic acid sequence data from several detection apparatus can be analyzed on the control computer and/or on a separate analysis computer. Thus, a central computer can be used for global analysis of nucleic acid sequence data from several different detection apparatus in a networked system.

Feedback mechanisms can be utilized in the control of several detection apparatus that form modules in a larger system. For example, quality control feedback loops can be used to observe parameters that are determinative or diagnostic of nucleic acid sequence data quality and appropriate responsive actions can be taken. Exemplary feedback loops that can be readily adapted for use in a modular sequencing system of the present disclosure are described, for example, in U.S. Pat. No. 7,835,871, which is incorporated herein by reference. A control computer can be programmed to include feedback loops based on such parameters and responses to control the quality of output (e.g. quality of sequence data) for a network of detection apparatus.

Nucleic acid sequence data that is obtained from one or more detection apparatus that function as modules or nodes in a system can be analyzed in real time. The sequence data can be evaluated against a parameter, for example by comparing the real-time acquired nucleic acid sequence to a standard sequence. Based on the results of the comparison, a decision can be made as to whether or not to proceed with a sequencing procedure at one or more of the detection apparatus. For example, environmental samples or pathology samples can be sequenced using several modules in a sequencing system and the data output from the modules can be compared to known sequences for suspected contaminants or pathogens. Once sufficient data has been collected to determine presence or absence of a particular contaminant or pathogen, sequencing can be halted at one or more of the modules. Exemplary protocols for real time analyses that can be adapted to a networked system of the present disclosure are described in US 2011/0246084 A1, which is incorporated herein by reference. The data analysis and decision procedures exemplified above can be made in an entirely automated fashion without human intervention. For example, the procedures can be carried out on a control computer or other computer that is part of a networked system set forth herein.

Alternatively or additionally to being electronically networked, several detection apparatus that are physically co-located in a rack can be networked with regard to delivery of samples and/or reagents. For example, cartridges can be delivered to appropriate detection apparatus using an autoloader or robotic device. Specifically, fluidic cartridges can be automatically removed from a storage location to appropriate detection devices. The automatic delivery can be under the instruction(s) of a control computer or other computer that is networked to the sequencing system. Furthermore, in some embodiments not all of the reagents used in a nucleic acid sequencing process need be contained in the fluidic cartridges that are used in a sequencing system. Rather, several detection apparatus can be in fluidic communication with one or more reservoirs containing bulk reagents. In this case, reagents can be delivered to several detection apparatus from a central fluidic storage location, for example, using a central fluid delivery system. Delivery of reagents can be under the instruction(s) of a control computer or other computer that is networked to a central fluid delivery system or that is networked to individual detection apparatus in the sequencing system.

Several embodiments of the present invention have been set forth herein in the context of nucleic acid sequencing or using nucleic acid sequencing applications as an example. However, the apparatus and methods set forth herein are not limited to nucleic acid sequencing applications. Other applications are useful as well including, but not limited to, other types of nucleic acid analyses such as those that utilize optically detected labels. Two examples are expression analyses carried out on nucleic acid arrays and genotyping analyses carried out on nucleic acid arrays. In either case, a microfluorometer, read head or detection apparatus set forth herein can be used for detection of the arrays. Furthermore, the arrays can be included in a fluidic cartridge and fluidically manipulated by appropriate modification of the fluidic cartridge and methods set forth herein. Exemplary array-based methods that can be modified for use with the apparatus and methods of the present disclosure include for example those described in US 2003/0108900, US 2003/0215821 or US 2005/0181394, each of which is incorporated herein by reference.

Other solid phase assays that are carried out on arrays or in multi-well substrates, such as enzyme-linked immunosorbent assays (ELISAs), can also be used in methods and apparatus set forth herein. Formats that use fluorescent labels are particularly useful since the labels can be detected using microfluorometers, read heads or detection apparatus set forth above. Furthermore reagents used in ELISAs or other solid phase assays can be processed in a fluidic cartridge similar to those set forth herein.

Methods and apparatus set forth herein can also be useful for monitoring the synthesis of molecules that are optically detectable or molecules that are prepared using optically detectable reagents, intermediates or side products. Polymeric molecules that undergo cyclic reactions are particularly applicable. For example, synthesis of nucleic acids or polypeptides both utilize optically detectable blocking groups or intermediates that can be detected using a microfluorometer, read head or detection apparatus set forth herein. Fluidic steps involved in synthetic protocols can be carried out in a fluidic cartridge similar to those set forth herein.

Another useful application of the methods and apparatus set forth herein is microscopic imaging of objects such as biological samples. Particularly well suited samples are tissues or cells. The samples can be presented on a substrate and detected as exemplified herein for nucleic acid arrays. Imaging of fluorescent properties of objects, such as biological samples, is particularly applicable to the methods and apparatus set forth herein. Microfluorometers can be used for such applications and optionally fluidic manipulations, for example, to introduce fluorescently labeled reagents, such as fluorescent tags for target molecules, can be performed.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection unless the context clearly dictates otherwise.

Although the invention has been described with reference to the examples provided above, it should be understood that various modifications can be made without departing from the invention. Accordingly, the invention is limited only by the claims.

What is claimed is:

1. A cartridge comprising:
   a housing comprising a material that is optically opaque, the housing further comprising a reception area for receiving a flow cell, wherein the housing holds:
   a plurality of reagent reservoirs, and
   a waste reservoir;
   a first rotary reagent selection valve positioned upstream of the reception area, the first rotary reagent selection valve including a plurality of input ports in respective fluid communication with a corresponding reagent reservoir of the plurality of reagent reservoirs, a reagent reservoir output port in selective fluid communication with the flow cell responsive to the flow cell being received in the reception area of the housing, the first rotary valve having a first position to allow liquid flow from a first reagent reservoir of the plurality of reagent reservoirs to the flow cell when the flow cell is in the reception area of the housing and to restrict liquid flow from a second reagent reservoir of the plurality of reagent reservoirs, and having a second position to allow liquid flow from the second reagent reservoir of the plurality of reagent reservoirs to the flow cell when the flow cell is in the reception area of the housing and to restrict liquid flow from the first reagent reservoir of the plurality of reagent reservoirs; and a second rotary reagent selection valve positioned downstream of the reception area, the second rotary reagent selection valve including an input port in selective fluid communication with the flow cell responsive to the flow cell being received in the reception area of the housing and a plurality of output ports, one of the plurality of output ports being in selective communication with the waste reservoir, and each other of the plurality of output ports being in selective communication with a respective one of the plurality of reagent reservoirs to create reagent loops with a single flow direction.

2. The cartridge of claim 1 further comprising a pump positioned downstream of the reception area of the housing and upstream of the second rotary reagent selection valve.

3. The cartridge of claim 1, further comprising a third reagent selection valve including a plurality of input ports in respective fluid communication with a corresponding reagent reservoir of a second plurality of reagent reservoirs and a reagent reservoir output port in selective fluid communication with an input port of the first rotary reagent selection valve.

4. The cartridge of claim 3, wherein at least one of the first plurality of reagent reservoirs or the second plurality of reagent reservoirs comprise sequencing by synthesis reagents.

5. The cartridge of claim 3, wherein at least one of the first plurality of reagent reservoirs or the second plurality of reagent reservoirs comprise amplification reagents.

6. The cartridge of claim 1 further comprising a sample reservoir, the sample reservoir in selective fluid communication with the flow cell responsive to the flow cell being received in the reception area of the housing.

7. The cartridge of claim 6, wherein the sample reservoir is selectively fluidically couplable to a single channel of the flow cell responsive to the flow cell being received in the reception area of the housing.

8. A cartridge comprising:
a housing comprising a material that is optically opaque, the housing further comprising a reception area for receiving a flow cell, wherein the housing holds a plurality of reagent reservoirs;

a first rotary reagent selection valve positioned upstream of the reception area, the first rotary reagent selection valve including a plurality of input ports in respective fluid communication with a corresponding reagent reservoir of the plurality of reagent reservoirs, a reagent reservoir output port in selective fluid communication with the flow cell responsive to the flow cell being received in the reception area of the housing, the first rotary valve having a first position to allow liquid flow from a first reagent reservoir of the plurality of reagent reservoirs to the flow cell when the flow cell is in the reception area of the housing and to restrict liquid flow from a second reagent reservoir of the plurality of reagent reservoirs, and having a second position to allow liquid flow from the second reagent reservoir of the plurality of reagent reservoirs to the flow cell when the flow cell is in the reception area of the housing and to restrict liquid flow from the first reagent reservoir of the plurality of reagent reservoirs; and a second rotary reagent selection valve positioned downstream of the reception area, the second rotary reagent selection valve including an input port in selective fluid communication with the flow cell responsive to the flow cell being received in the reception area of the housing and a plurality of output ports in selective communication with a respective one of the plurality of reagent reservoirs to create reagent loops with a single flow direction.

9. The cartridge of claim 8 further comprising a pump positioned downstream of the reception area of the housing and upstream of the second rotary reagent selection valve.

10. The cartridge of claim 8, further comprising a third reagent selection valve including a plurality of input ports in respective fluid communication with a corresponding reagent reservoir of a second plurality of reagent reservoirs and a reagent reservoir output port in selective fluid communication with an input port of the first rotary reagent selection valve.

11. The cartridge of claim 10, wherein at least one of the first plurality of reagent reservoirs or the second plurality of reagent reservoirs comprise sequencing by synthesis reagents.

12. The cartridge of claim 10, wherein at least one of the first plurality of reagent reservoirs or the second plurality of reagent reservoirs comprise amplification reagents.

13. The cartridge of claim 8 further comprising a sample reservoir, the sample reservoir in selective fluid communication with the flow cell responsive to the flow cell being received in the reception area of the housing.

14. The cartridge of claim 13, wherein the sample reservoir is selectively fluidically couplable to a single channel of the flow cell responsive to the flow cell being received in the reception area of the housing.

* * * * *